United States Patent
Scott et al.

(10) Patent No.: US 11,465,145 B2
(45) Date of Patent: Oct. 11, 2022

(54) METHOD AND SYSTEM FOR SAMPLE COLLECTION, STORAGE, PREPARATION AND DETECTION

(71) Applicant: MicroGEM International Plc, Southampton (GB)

(72) Inventors: Orion Scott, Charlottesville, VA (US); Christopher Birch, Charlottesville, VA (US); Daniel Mills, Charlottesville, VA (US); Brian Root, Charlottesville, VA (US); James Landers, Charlottesville, VA (US); Jingyi Li, Charlottesville, VA (US); Matthew Yeung, Mount Waverley (AU); David Saul, Dunedin (NZ); David Vigil, Mount Waverley (AU); Andrew Guy, Mount Waverley (AU); Stan Wada, Mount Waverley (AU); Betina De Gorordo, Mount Waverley (AU); Steward Dodman, Mount Waverley (AU); Tom Moran, Southampton (GB); Stuart Knowles, Mount Waverley (AU); Fernando Dias, Mount Waverley (AU); Rick Gardner, Mount Waverley (AU)

(*) Notice: Subject to any disclaimer, the term of this patent is extended or adjusted under 35 U.S.C. 154(b) by 0 days.

(21) Appl. No.: 17/412,354

(22) Filed: Aug. 26, 2021

(65) Prior Publication Data
US 2022/0088601 A1 Mar. 24, 2022

Related U.S. Application Data
(60) Provisional application No. 63/170,147, filed on Apr. 2, 2021, provisional application No. 63/111,859, filed
(Continued)

(51) Int. Cl.
*B01L 3/00* (2006.01)
*G01N 33/569* (2006.01)
(Continued)

(52) U.S. Cl.
CPC ... *B01L 3/502738* (2013.01); *B01L 3/502715* (2013.01); *B01L 3/502761* (2013.01);
(Continued)

(58) Field of Classification Search
CPC ........ B01L 3/00; B01L 7/00; B01L 3/502723; B01L 3/50273; B01L 3/502738;
(Continued)

(56) References Cited

U.S. PATENT DOCUMENTS 8,324,372 B2 * 12/2012 Brahmasandra ..... C12Q 1/6813
536/25.4
9,988,676 B2 6/2018 Egan et al.
(Continued)

FOREIGN PATENT DOCUMENTS

WO 2016144192 9/2016
WO WO-2017066485 A1 * 4/2017 .......... B01L 3/50273

OTHER PUBLICATIONS

Xu et al., A self-contained all-in-one cartridge for sample preparation and real-time PCR in rapid influenza diagnosis Issue 22, 2010, Lab on a Chip (Abstract).

*Primary Examiner* — Brian J. Sines
(74) *Attorney, Agent, or Firm* — Porzio Bromberg & Newman P.C.

(57) ABSTRACT

A collection device for a biological sample to capture target compounds such as viruses or other pathogens or particles for testing from within the sample and move the captured target compound to a separate chamber for subsequent processing. The collection device can include an openable substance blister including capture particles located in a cup
(Continued)

interior. Capture particles can attract and bind the target compounds from the sample. An extraction tube extracts any nucleic acid from the target compound for storage or subsequent amplification and testing to confirm presence of known microorganisms. The extraction tube can comprise a heat-deformable material and can be connected to a microfluidic cartridge for further processing of nucleic acid including, amplification and detection. The microfluidic cartridge includes valves and a plurality of chambers for amplification.

17 Claims, 26 Drawing Sheets

Related U.S. Application Data on Nov. 10, 2020, provisional application No. 63/080,210, filed on Sep. 18, 2020.

(51) Int. Cl.
| | |
|---|---|
| G01N 33/543 | (2006.01) |
| G01N 1/18 | (2006.01) |
| G01N 1/40 | (2006.01) |
| B01L 7/00 | (2006.01) |
| C12Q 1/6806 | (2018.01) |
| G01N 1/10 | (2006.01) |
| C12Q 1/686 | (2018.01) |

(52) U.S. Cl.
CPC .............. *B01L 7/52* (2013.01); *G01N 1/18* (2013.01); *G01N 1/4022* (2013.01); *G01N 33/54326* (2013.01); *G01N 33/56983* (2013.01); *B01L 2200/027* (2013.01); *B01L 2200/04* (2013.01); *B01L 2200/10* (2013.01); *B01L 2300/044* (2013.01); *B01L 2300/0832* (2013.01); *B01L 2300/0864* (2013.01); *B01L 2300/18* (2013.01); *B01L 2400/0622* (2013.01); *C12Q 1/686* (2013.01); *C12Q 1/6806* (2013.01); *G01N 2001/1056* (2013.01); *G01N 2333/165* (2013.01); *G01N 2800/26* (2013.01)

(58) Field of Classification Search
CPC .............. B01L 3/5027; B01L 3/502715; B01L 3/502761; B01L 2300/18; B01L 2400/0622; B01L 7/52; B01L 2300/0832; B01L 2300/0864; B01L 2200/027; B01L 2200/04; B01L 2200/10; C12Q 1/68; C12M 1/00; G01N 1/18; G01N 2001/1056; G01N 1/4022; G01N 2800/26; G01N 33/54326; G01N 33/56983

See application file for complete search history.

(56) References Cited

U.S. PATENT DOCUMENTS

| 10,758,900 B2 | 9/2020 | Saul | |
| 2009/0131650 A1* | 5/2009 | Brahmasandra | ..... C12Q 1/6813 536/25.4 |
| 2009/0253181 A1* | 10/2009 | Vangbo | ............... B01L 3/50273 435/91.1 |
| 2014/0295441 A1 | 10/2014 | Egan et al. | |
| 2018/0304253 A1* | 10/2018 | Landers | .................. C12Q 1/00 |

* cited by examiner

FIG. 11A-E

METHOD AND SYSTEM FOR SAMPLE COLLECTION, STORAGE, PREPARATION AND DETECTION

This invention was made with government support under Contract Number: 75N92020C00015 awarded by National Institutes of Health (NIH). The government has certain rights in the invention.

FIELD OF THE INVENTION

The invention relates to a means of capturing bodily fluid for subsequent storage, particle capture and nucleic acid extraction. The invention also relates to a microfluidic detection cartridge configured to engage with an extraction tube and configured for carrying out thermocycling for amplification and detection of nucleic acid. The cartridge is further configured to be part of an overall device assembly which controls the processes of sample preparation, extraction, thermocycling, cooling and detection analysis which can be used at point-of-care to deliver rapid results in a variety of settings.

DESCRIPTION OF THE RELATED ART

Conventional techniques have been described for obtaining a sample to be tested. Problems to be overcome from conventional techniques include:
Ensuring the correct amount of sample is obtained, i.e. the user does not flood the system or provide an inadequate biological sample, and that it is retained securely in a container for ease of use by a non-medically trained user.
Ensuring the required components to prepare the sample and allow for nucleic acid extraction are safely stored and housed within the device (undamageable), able to mix with the sample to perform their function adequately at the right stage of the process, including target compound capture and obtaining the correct sample consistency.
Ensuring adequate mixing of the components with the sample without possible interruption by user.
Ensuring efficient and fast movement of the sample through the device to the attached nucleic acid extraction chamber.
Eliminate potential for contamination at extraction and all subsequent analysis stages.

Known microfluidic thermocycling PCR devices include a conventional cartridges known in the art and a heat-deformable extraction tube.

US2014295441AA and U.S. Pat. No. 9,988,676B2 describe a microfluidic cartridge for use analyzing nucleic acid in a biological sample. A cartridge interface module which engages with the microfluidic cartridge, a nucleic acid analyzer, a collection, storage and extraction system and polymerase chain reaction (PCR) assembly component which can separate nucleic acid and detect fragments optically. Cartridge and sample connection is via a perpendicular orientation.

"A self-contained all-in-one cartridge for sample preparation and real-time PCR in rapid influenza diagnosis" Issue 22, 2010, Lab on a Chip describes a cartridge as part of a miniaturized automated diagnosis system where a sample is pipetted into the cartridge, the sample preparation and analysis taking 2.5 hours. FIG. 16 shows an image of this prior art cartridge.

Many other microfluidic cartridges are well known in the art which are configured for use with a detection device.

It is desirable to provide a suitable collection device for a biological sample, particularly saliva, where the device can capture any potential viruses or other particles and target compounds within the sample and move these to a separate chamber within the device for subsequent use and the separate chamber being a chamber capable of nucleic acid extraction.

It is desirable to provide a microfluidic device to ensure all sample fluid is transported out of the tube, into the cartridge, safely and securely for accurate nucleic acid amplification and detection and that all parts are manufacturable on a rapid and sizeable scale.

SUMMARY OF THE INVENTION

The invention relates to a collection device for a biological sample, particularly saliva, where the device captures potential viruses or other target particles and compounds for testing from within the sample and moves the captured target compounds to a separate chamber for subsequent use. The separate chamber being a chamber capable of nucleic acid extraction. In one embodiment, an extraction tube is used to extract the viral nucleic acid from the sample for storage or subsequent testing of the nucleic acid to confirm the presence of known microorganisms in a clinical or non-clinical setting.

The collection device can include a diluent blister located in a cup interior. An attachable cap can be associated with the cup. The diluent blister can be opened automatically or manually with an action of the cap by one of several mechanisms including bursting, tearing, ripping or squeezing open the diluent blister. In one embodiment, the diluent blister is pierced open by a piercing means within the cap in which a twist closure mechanism of the cap causes the piercing means to tear open a pierceable portion of the blister. Capture particles such as magnetic beads can also be housed with the diluent within the diluent blister. In one embodiment, the pierceable portion is a foil sheet of the diluent blister, which is torn open by a bladed edge, twist mechanism within the cap. The diluent avoids clumping of a saliva sample and improves binding. A sample can be stored and secured within the collection device to ensure automatic incorporating into the sample together with the capture particles. The capture particles can be housed within the diluent blister in the cup or elsewhere within the cup or cap. When mixed with the sample, the capture particles can bind proteins from the sample. Suitable capture particles include magnetic beads of various brands, namely any magnetic enrichment bead or other particles capable of compound capture and can be lyophilised, coated or uncoated.

The collection device can be configured to ensure the diluent is only released at the appropriate time such as when the sample is no longer hazardous. The cap may be un-removable once connected to the collection device. For medical sample capture, the cap is un-openable so that user is unable to interfere with the process. The twist option can be preferable to a snap closure mechanism to prevent interfering with the collected sample.

In an embodiment, a nest within the cap may hold and store a positive control pellet or process control substance. An example control pellet includes a bacterial phage within a lyophilised pellet.

The control pellet nest can sit directly below the base of a plunger, when the plunger is in a first, un-plunged position within the cap. The control pellet provides a positive control inclusion to provide confirmation that a sample has been processed so that a user knows that the device is functional. The control pellet can be located within a nest or other suitable holding means. Inclusion of a control pellet directly below the base of the plunger ensures that the lyophilised control pellet dissolves in the liquid when the diluent blister is opened and the first mixture moves to the base of the upper compartment. In the present invention, the user may be required to shake, swirl or similarly motion or agitate the device via a variety of appropriate methods after the cap is closed, to facilitate the dissolving of the control pellet as well as mixing of the abovementioned capture particles with the sample. Alternatively, no control pellet or nest is required at the sample collection stage, and a positive control is included downstream, to confirm the functionality of the device and process.

The collection device can be activated by various technologies. In one embodiment, the plunger can be positioned in a body of the attachable cap. An instrument actuates a rod that pushes the plunger from a first position into a plunged position. The action prevents premature plunging by the user, for example before adequate mixing and/or target compound capture has occurred. The collection device is device-lead rather than user-lead. The plunger can be a hidden mechanism within the body of the cup, which is hidden from the user and pre-assembled to prevents accidental interference. The plunger can provide an airtight seal at the top of the cap. The base of the plunger is flat to provide contact with the magnet cage top.

The present invention provides an automated process with possible pauses in the automated process to allow for time-sensitive actions to occur including adequate mixing of capture particles with sample and optionally positive control mixing to form an enriched sample. The present invention ensures both a liquid-tight seal at the top of the device for preventing spillage of potentially biohazardous waste if the device is swirled and also provides a liquid-tight seal within the base of a lower compartment for preventing sample and other fluid entering the extraction tube or other downstream device, together with the magnet which could inhibit the downstream assay. In one embodiment, the plunger, when activated from a first position to an initial plunged position, can act to simultaneously and automatically contact a sharp edged face to open a foil barrier situated at the base of an upper compartment, this opening of the foil barrier can allow a substance through to a lower compartment, where a magnet can be situated. The plunger can pause in the initial plunged position, before moving to a further plunged position, which can act to push the magnet further through to the attached extraction tube. Simultaneously, the plunger is used to liquidly seal the base of the lower compartment and the top of the cap. The plunger can go directly from a first position to the further plunged position.

In an embodiment, a wiping means can be included within the lower portion of the device. The wiping means can be used to remove fluid or substance from a magnet as it is pushed by the plunger down and through into an attached extraction tube. In one embodiment, the wiping means can be a plurality of separate medical grade sponges cut to shape or can be one continuous sponge element. The wiping means can be used or added as an extra precaution to prevent the saliva sample being brought down into the extraction tube, where it may inhibit the downstream assay or process. The wiping means can also be used to create a seal to prevent excess saliva sample spilling through. In alternative embodiments, the wiping means can be any material including bristles, rubber wipers and/or felt strip surrounding the outer rim of the exit opening. Wiping means are not essential for all embodiments and can be dependent on sample type.

In one embodiment, the cup can have a general funnel shape and tapered in an upright orientation. This helps ensure that the sample collection travels downwards due to gravity and the tapered shape ensures saliva and magnetic beads are funnelled down close to the magnet in the lower compartment so that the magnetic beads can capture the virus faster in the upper compartment and magnet attraction can occur faster in the lower compartment.

The present invention provides a non re-openable closure mechanism for the cap. The cap is designed to lock so no interference from a user and safety of the user from sample and compounds. The extraction tube attachment means can be used for ease of assembly. In one embodiment, the extraction tube attachment means is designed to be able to be slotted together and provided to the end user as one piece for user convenience.

In one embodiment, a cap closure mechanism can be a snap or thread mechanism. A fill line provided on the cup can provide accuracy and to guide user to obtain an adequate and sufficient sample.

In one embodiment, a magnet cage is used to house the magnet used to isolate the magnetic beads from the sample. The magnet cage may be held within a press-fit within the lower compartment. The magnet cage can act to prevent magnetic beads from becoming detached from the magnet which, is pushed down from the lower compartment into an extraction tube. An alternative embodiment to a magnet cage is a modified magnet which fits where the cage otherwise would. This removes the need for the magnet cage.

The collection device can be used in a non-clinical and non-medical environment by both medical/clinical professionals and non-medical professionals whilst ensuring the sample is adequately prepared for efficient nucleic acid extraction to occur. Example users of the technology include but are not limited to: medical professionals, field-based diagnostics, dentist surgeries, venue owners, schools, airports, and certain hospital units.

The invention relates to a microfluidic cartridge for nucleic acid extraction, amplification and detection. In one embodiment, the cartridge comprises a valve unit comprising a plurality of units within a junction each of the plurality of units connected to a ring-shaped valve. The valve unit can be a hydrophobic valve. The hydrophobic valve having a plurality of units has the function of preventing liquid flow, but allowing air though. This function is required to maintain the valve function. Liquid can also be prevented from entering the ring-shaped valve by a means of capillary action.

The valve unit can be a hydrophobic valve including a plurality of units connected to a main ring-shaped valve. In one embodiment the hydrophobic valve is an eight-way hydrophobic valve comprising eight units connected to the main ring-shaped valve. Each of the eight units is in individual fluid connection with an amplification chamber and with the ring-shaped valve. At least a portion of the junction of the plurality of units can be covered by a hydrophobic sheet, membrane or filter. The valve closure can be controlled by a control device in which the cartridge can be inserted.

The cartridge contains a plurality of microfluidic channels configured for moving a sample fluidically throughout. The microfluidic channels being in fluid communication with one or more sample inlets and in fluid communication with a plurality of fillable chambers for amplification or other processing of a sample. The chambers can be configured to perform nucleic acid amplification and analysis.

The cartridge can be configured to include an interface with an extraction tube for introducing a sample. The interface comprising a channel and polymer filter at the base of the cartridge entrance situated within a bore within the cartridge body. The interface can be surrounded by a Luer taper connector. This configuration prevents any leak of biohazardous fluid to outside of the device hardware. Placing the polymer filter within the cartridge also allows for storage within a dried environment for the cartridge and filter.

The orientation is such that the extraction tube sits within the same plane as the cartridge in a co-axial relationship, the cartridge and tube to be positioned "upright" in the control device with the extraction tube parallel to the vertical plane of the cartridge. This configuration provides that both the tube and cartridge contents will be influenced by gravity when the cartridge is orientated vertically. A tube made from a heat-deformable material such as a heat-deformable polymer, comprising the extraction reagents, can provide a sufficient pressure source, when heated, to facilitate fluidic movement, and force a sample through to the amplification chambers, also stacked in the same vertical plane as the cartridge, moving the sample upwards through the microfluidic channels, against the gravitational force. An example of a heat-deformable extraction tube is described in U.S. Pat. No. 10,758,900 or WO16144192 A1 hereby incorporated by reference in its entirety into this application. This configuration also strengthens the device connection and provides increased compactness for users.

In use, the cartridge can be configured to be part of a device including an extraction tube connected to the sample capture means. The sample capture means can be the collection device. The upstream fluidics includes an internal magnet directly contacting magnetic capture particles carrying a sample or substance, bringing the sample to the extraction tube which provides a means to force the extracted nucleic acid through to the cartridge microfluidic channels. The magnet and upstream plunger process can be controlled by a control device and may include a pusher piston or rod as well as heating elements and optical means.

The cartridge is configured to be insertable into a control device for controlling detection and analysis of a sample, and removeable and disposable once the process is complete. The cartridge can be inserted into a control device by the user, locked during the required process such as the PCR process and removed by the user and disposed of when the process is complete in biohazardous waste. The device may include a locking means to prevent interruption or cartridge removal at an incorrect time. The device may include means for identifying a result as inaccurate or corrupted if user interruption occurs at an incorrect time.

The invention will be more clearly described by reference to the following drawings.

DETAILED DESCRIPTION

Figure 1:
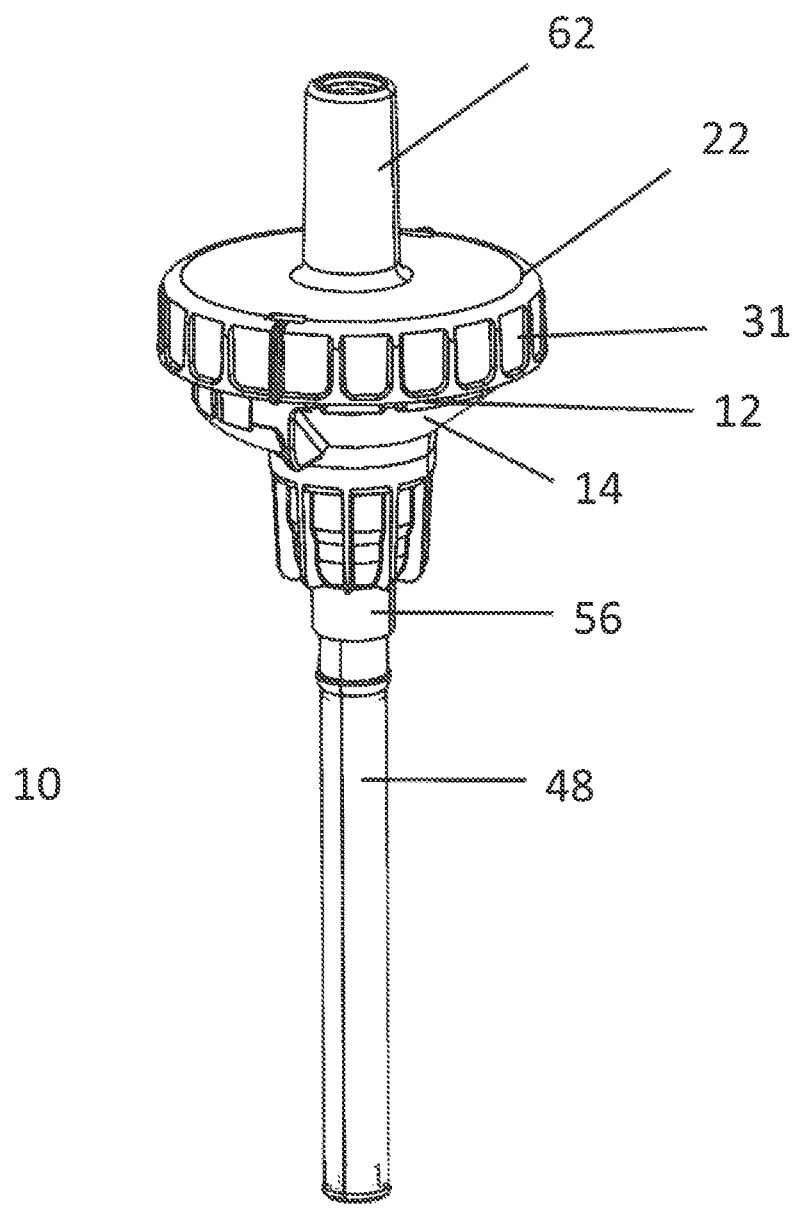
FIG. 1 shows a perspective view of an embodiment of the invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIGS. 1-9 illustrate collection device 10 in accordance with the teachings of the present invention. Cup 12 is comprised, in certain preferred embodiments, of a tapered upper compartment 14 into which a saliva sample is collected from a patient. In a preferred embodiment, 0.25-2 mL collection is provided in upper compartment 14 to an optional fill line 15 marked on a perimeter of wall 16 of cup 12. Magnet cage 42 can be used to mark the fill-line 15.

In use, saliva sample collection is achieved by the user spitting, expelling saliva through their mouth, into opening 18 of cup 12. This is achieved by spitting directly into upper compartment 14 of cup 12. Once the required sample size is met, cap 22 is placed on cup 12 such as by the same user or a separate device handler. Cap 22 can be provided separately in separate packaging and may rest on collection cup 12 prior to use.

In the preferred embodiment, upper compartment 14 of cup 12 is tapered. Upper compartment 14 includes blister 24 filled with diluent 26. In a preferred embodiment, capture particles 28 with a means of capturing target compounds such as viruses and other pathogens or biological targets, are also stored in upper compartment 14, preferably within the diluent within the blister 24. Capture particles 28 can be magnetic beads within lyophilised or unlyophilised pellets. In use, the beads are capable of capturing virus from within a sample which is achieved within a short time frame which can preferably be within 5 200 seconds, optionally within 30-60 seconds. In a particularly preferred embodiment the target compounds which the magnetic beads can capture are biological pathogens including SARS-CoV-2 and Influenza Types A and B. When mixed with the sample, the magnetic beads capture and bind the target compounds. Suitable capture particles include any coated or uncoated, lyophilised or unlyophilised magnetic beads or enrichment beads capable of compound capture.

Upper portion 30 of walls 16 of upper compartment 14 are capable of connecting with walls 31 of cap 22. In one embodiment, upper compartment 14 tapers down to a narrower diameter portion. A seal base 32 can separate the upper compartment 14 from a lower compartment 34. Above seal base 32 are flaps 36 which are closed and openable by the action of plunger 38. Preferably, flaps 36 comprise a snappable face, which, when contacted by plunger 38, snaps downwards acting to pierce seal base 32. This action opens upper compartment 14 to lower compartment 34 allowing the movement of the sample down to lower compartment 34. Seal base 32 can be formed of foil or other suitable sealing material.

A nest compartment 40 can be situated below plunger 38, when the plunger 38 is in the first, unplunged position within cap 22. When cap 22 is connected to upper compartment 12, nest 40, comprising pelleted substance 43 sits directly above flaps 36 in a closed position. Nest compartment 40 can include a plurality of claw features configured to hold a pelleted substance. Pelleted substance 43 can be, for example, a positive control or a required compound or substance to be mixed with or combined with the collected sample. In a preferred embodiment, the positive control is a bacterial phage.

Lower compartment 34 of cup 12 comprises magnet cage 42. Magnet cage 42 can house magnet 44. Magnet 44 can be a diametrically-poled magnet. Preferably, magnet 44 is moveably positioned within magnet cage 42 to allow for downward movement actuated by motion of plunger 38 through lower opening 46 of cup 12 and into attachment tube 48 for collection. In a preferred embodiment, attachment tube 48 is an extraction tube configured for carrying out nucleic acid extraction. In a preferred embodiment of use, magnet 44 attracts the magnetic capture particles 28 from the saliva sample having captured any virus or target compound. These capture particles will stay connected by magnetic attraction to magnet 44 allowing magnet 44 and capture particles 28 to be moved into attachment tube 48. The movement of the plunger 38 from an initial plunged position to a further plunged position will act to push the cage 42 and magnet 44 down through into the attachment tube 48 where it will fall freely within the attachment tube 48.

Optionally, pelleted substance 43 is not included. Seal base 32 or flaps 36 are not included and upper compartment 14 is open to lower compartment 34.

Below the magnet cage 42, the interior of the cup wall 49 can be coated in a wiping means 50 able to remove any sample from the magnet 44 or magnet cage 42 before the magnet and/or magnet cage is pushed down into the subsequent connected attachment tube 42 for storage or for extraction of nucleic acid from capture particles. Wiping means 50 can be a wiper coating of a plurality of separate materials or one continuous coating.

Optionally, in one embodiment, pelleted substance 43 is not included. Seal base 32 or flaps 36 are not included and upper compartment 14 is open to lower compartment 34. In this embodiment, below magnet cage 42, interior of cup wall 49 can be coated in wiping means 50.

Rim 54 of lower opening 46 of cup 12 includes a collar 56 to connect to an attachment tube 48 for storage or extraction or suitable processes. In a preferred embodiment, the connection of attachment tube 48 to cup 12 is completed during manufacturing stage, in an alternative embodiment attachment, attachment tube 48 may be provided to a user unconnected for the user themselves to connect. Collar 56 is a Luer connection taper or suitable medical standard for connecting interfaces.

Figure 2:
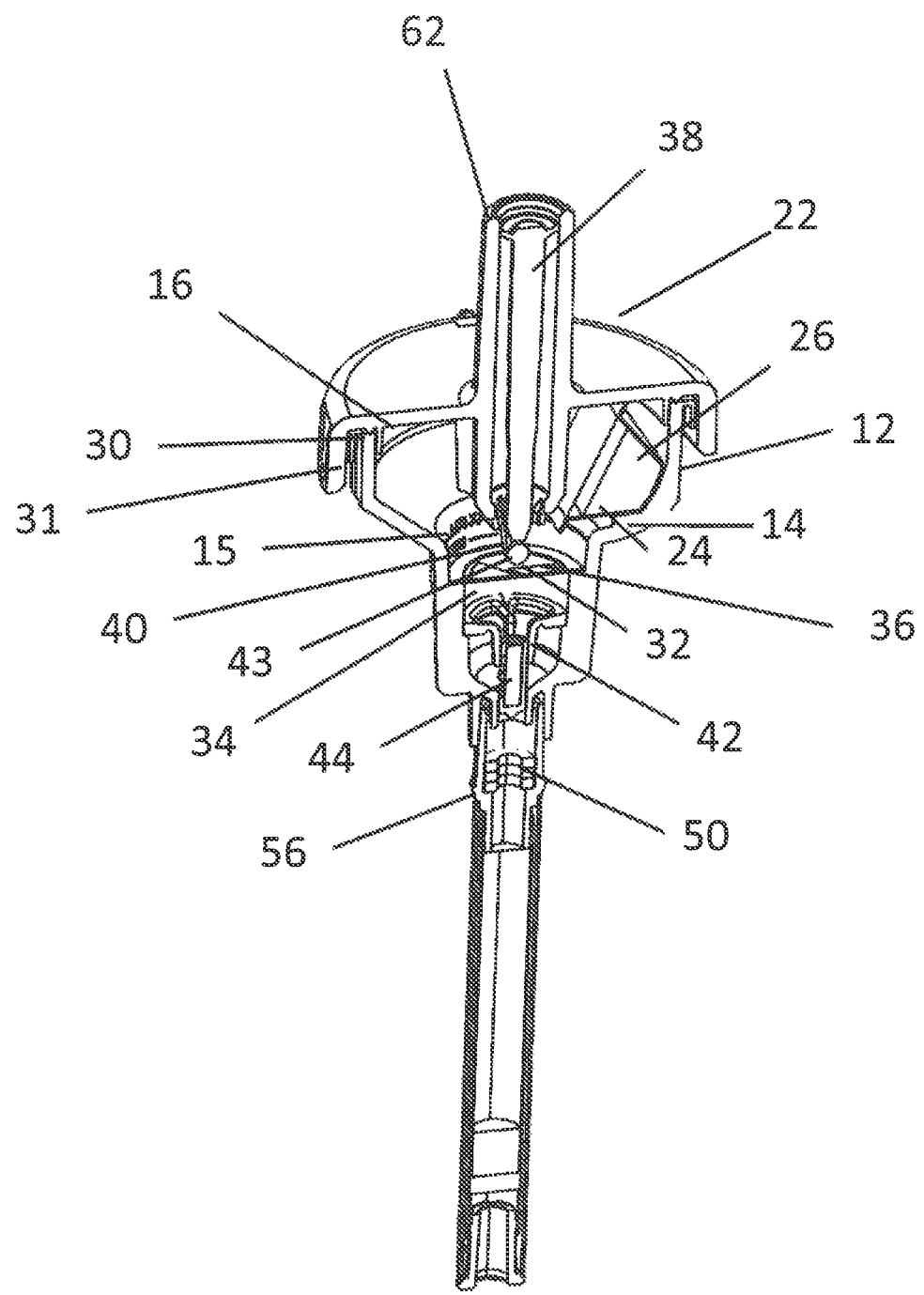
FIG. 2 shows an angled cross-section of the embodiment of FIG. 1.
Figure 3:
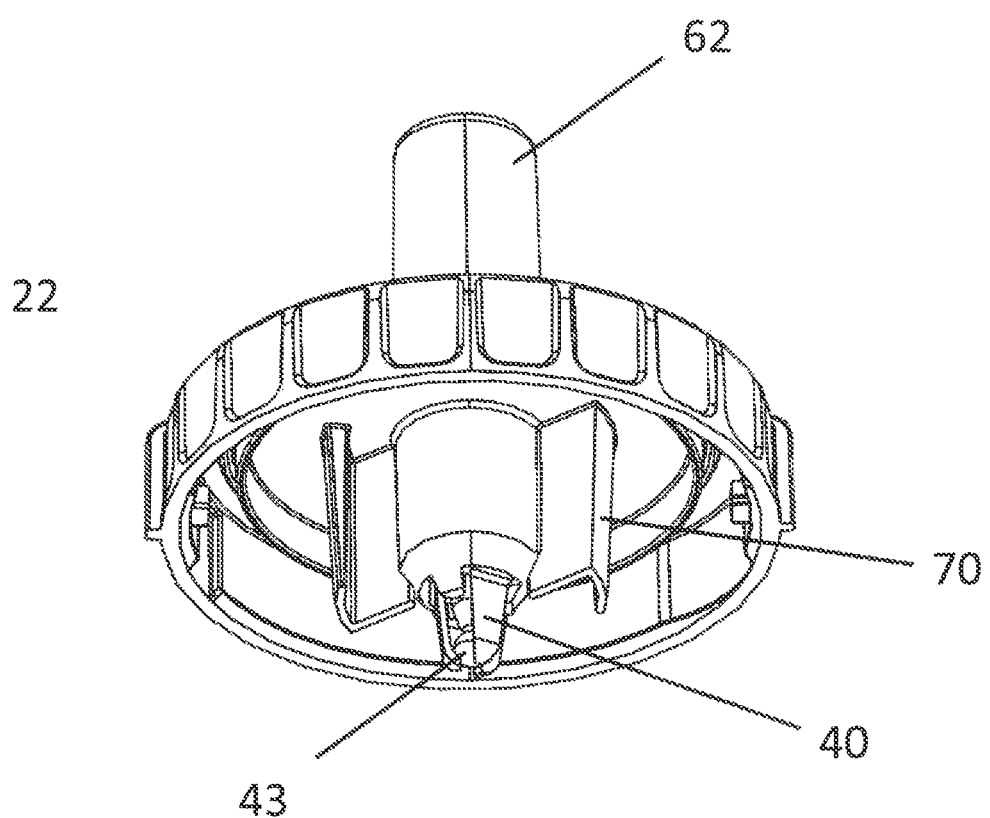
FIG. 3 shows a perspective view of an embodiment of the cap.
Figure 4:
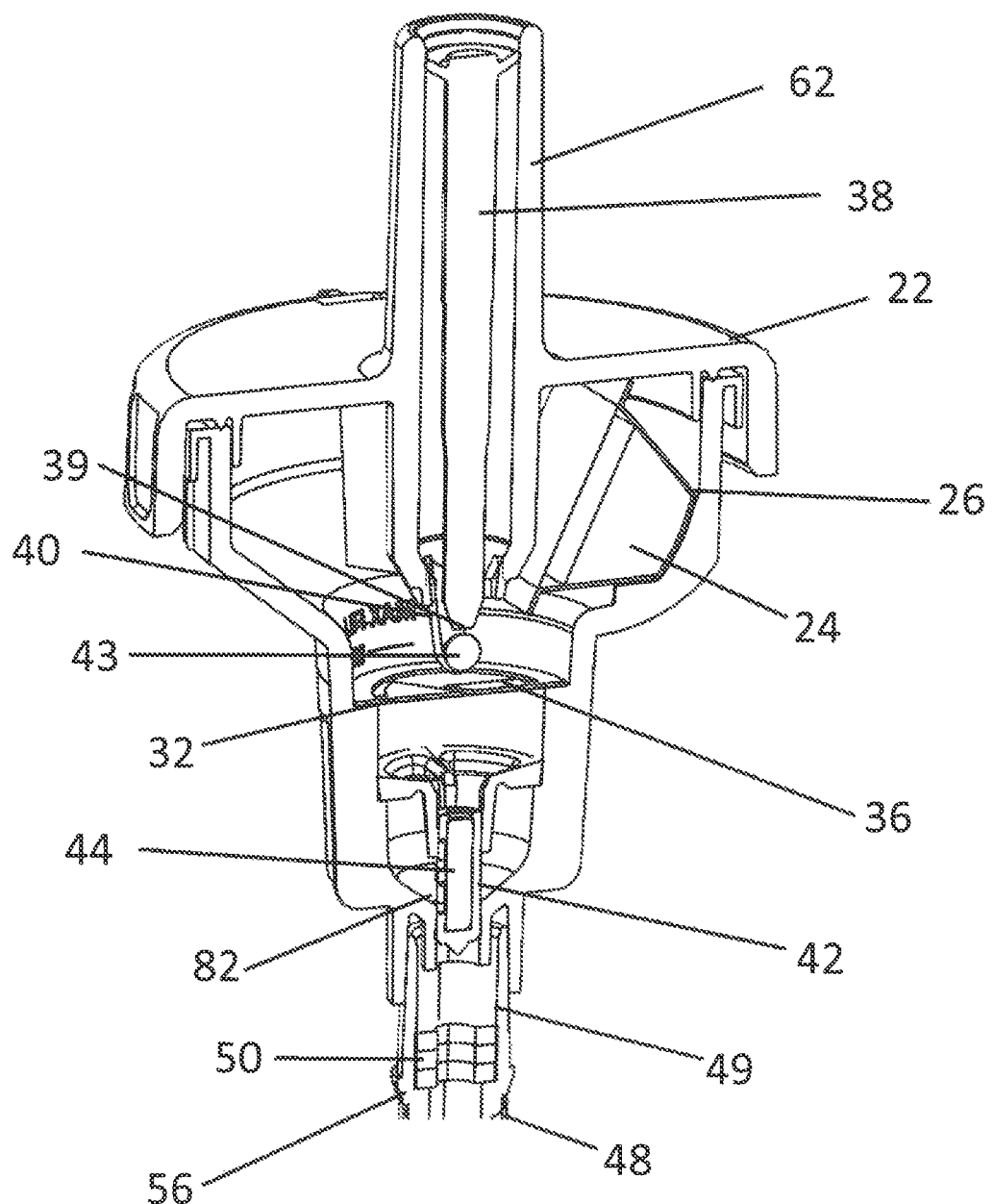
FIG. 4 shows a perspective cross-section view of the invention with the cap attached.
Figure 5:
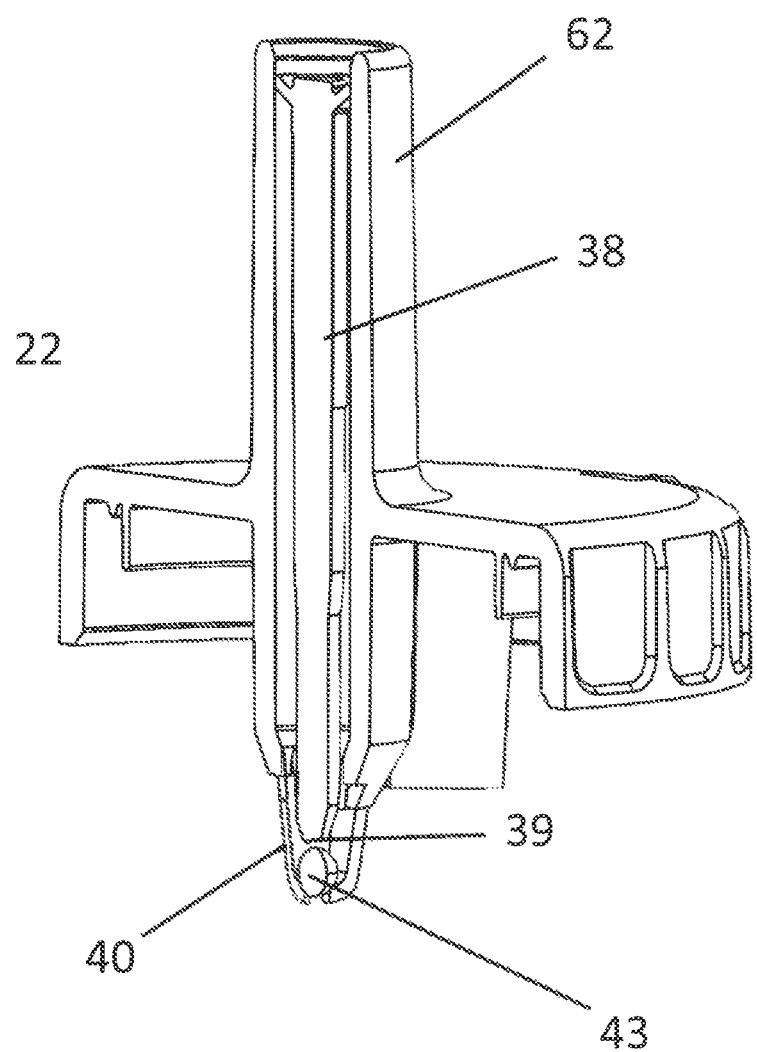
FIG. 5 shows a side, cross-section view of the cap showing the plunger.

Cap 22 comprises an exterior circular base 60 with central extruding portion 62 as shown in the FIGS. 1-8, in which plunger 38 is situated in a first unplunged position. Plunger 38 is not accessible to the user as it is housed and hidden within interior walls of extruding portion 62 of cap 22. This prevents accidental or premature activation by the user. In a preferred embodiment, plunger 38 is circular in diameter. In use, when cap 22 is placed and locked in position on cup 12, base 39 of plunger 38 rests just above closed flaps 36 as seen in FIG. 2 and FIG. 4. In a preferred embodiment, plunger 38 is cylindrical in diameter to enable smooth movement within the tapered narrow portion 82 of lower compartment 34 of the cup and acts to create an airtight seal when fully plunged the full length to be in the fully plunged position. The air-tight seal is formed between the outer perimeter 84 of plunger 38 and the inner perimeter of walls of the lower compartment 34, as exemplified in FIG. 9.

Plunger 38 preferably comprises a liquid-sealing portion at its top which acts to seal upper compartment and prevent spillage out of cup 12. Liquid-sealing portion can be a rubber layer.

In use, after collection of saliva sample within upper compartment 14, cap 22 is closed and secured onto upper opening 18 of cup 12 by a closure mechanism to be actioned by the user. In a preferred embodiment, cap 22 is not re-openable or unattachable once securely attached. The user-actioned, closure mechanism brings piercing mechanism 70 shown in FIG. 3, located within the interior of cap 22, into contact with the surface of the blister 24 filled with diluent 26 and capture particles 28 with a means of capturing virus causing piercing or tearing of blister 24 and triggering diluent 26 and particles with a means of capturing virus 28 to empty out of blister 24 and mix with the collected saliva sample within upper compartment 14. In the preferred embodiment, piercing mechanism 70 is a bladed edge and closure mechanism is a twist-action.

Figure 6:
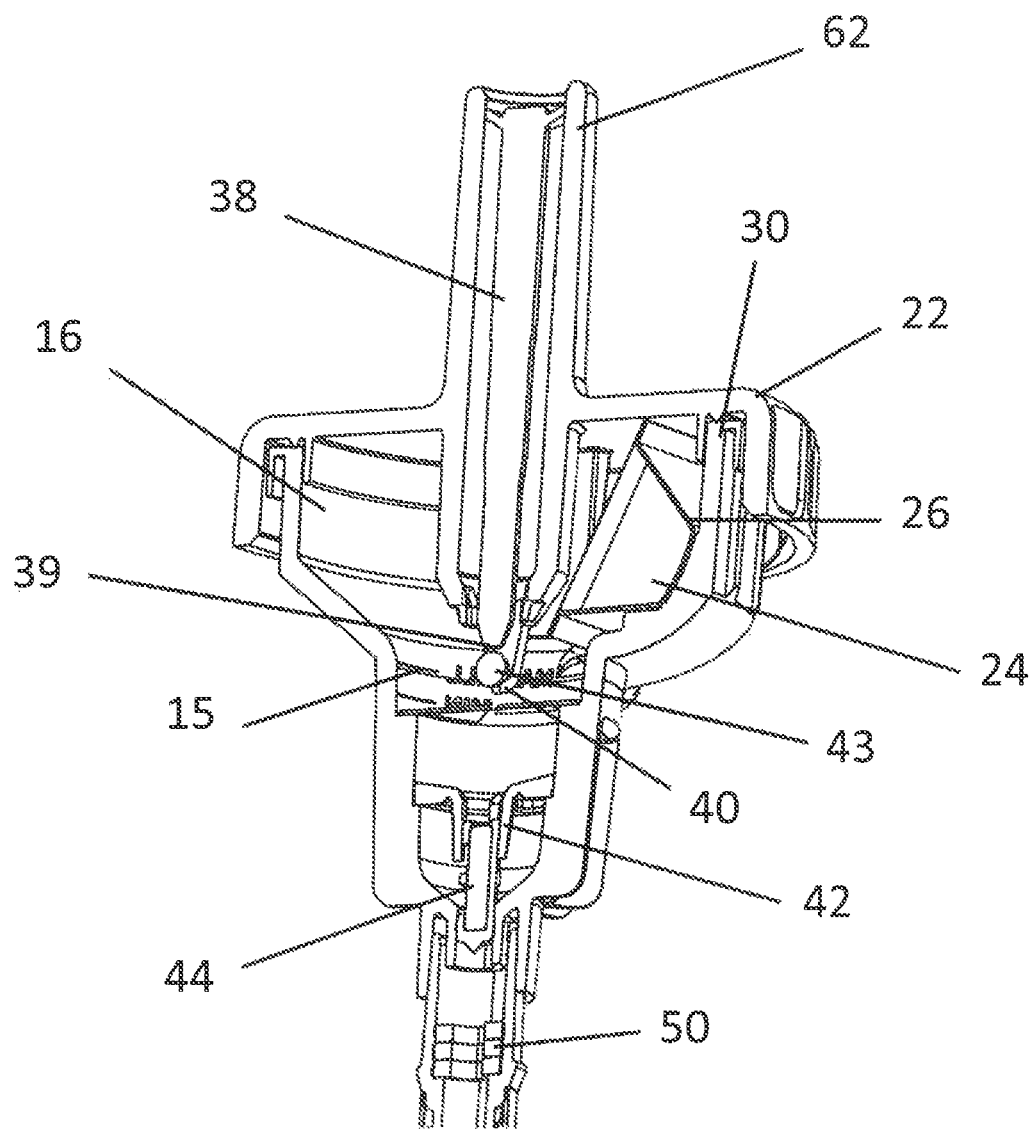
FIG. 6 shows a cross-section perspective view of the invention with the cap attached.
Figure 7:
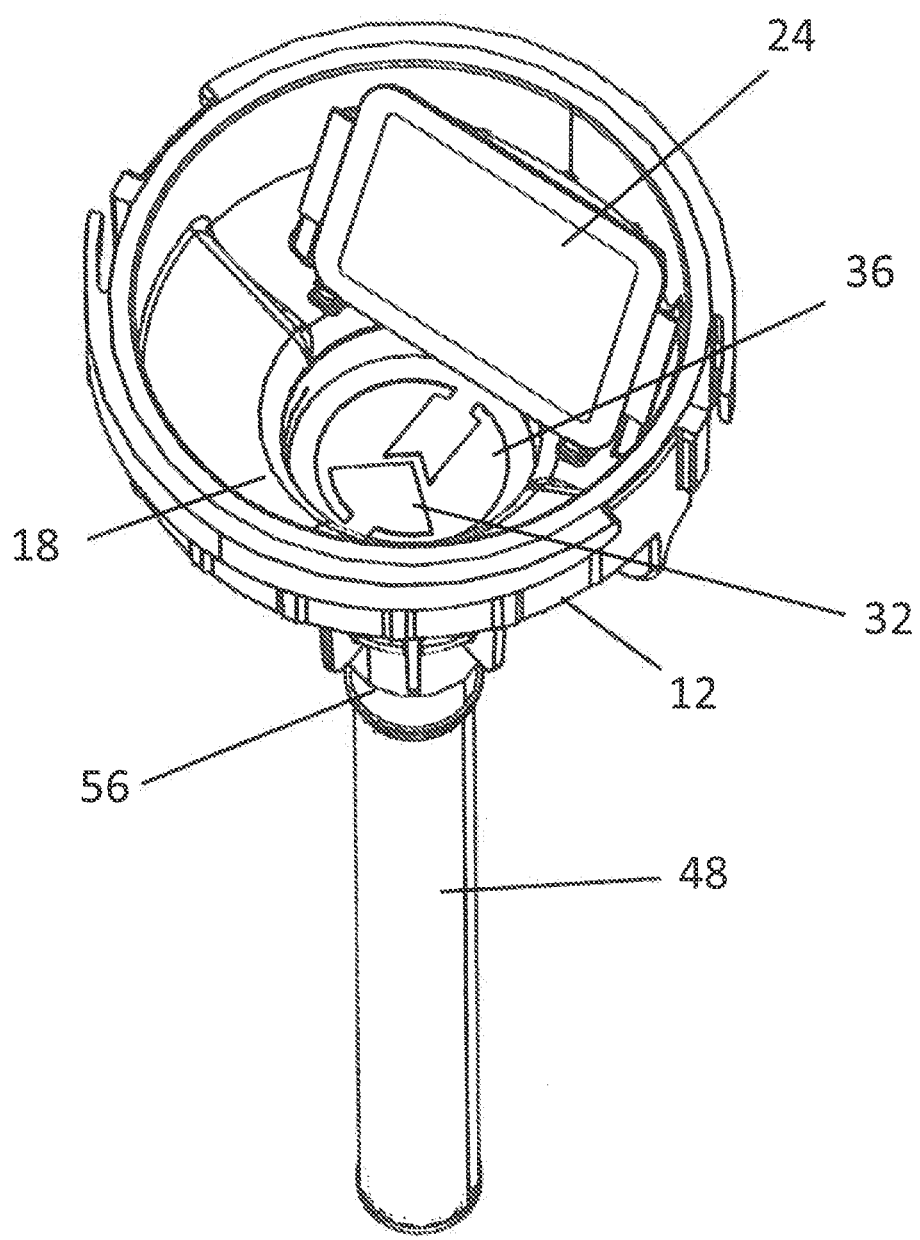
FIG. 7 shows a perspective view of the invention without the cap attached.
Figure 8:
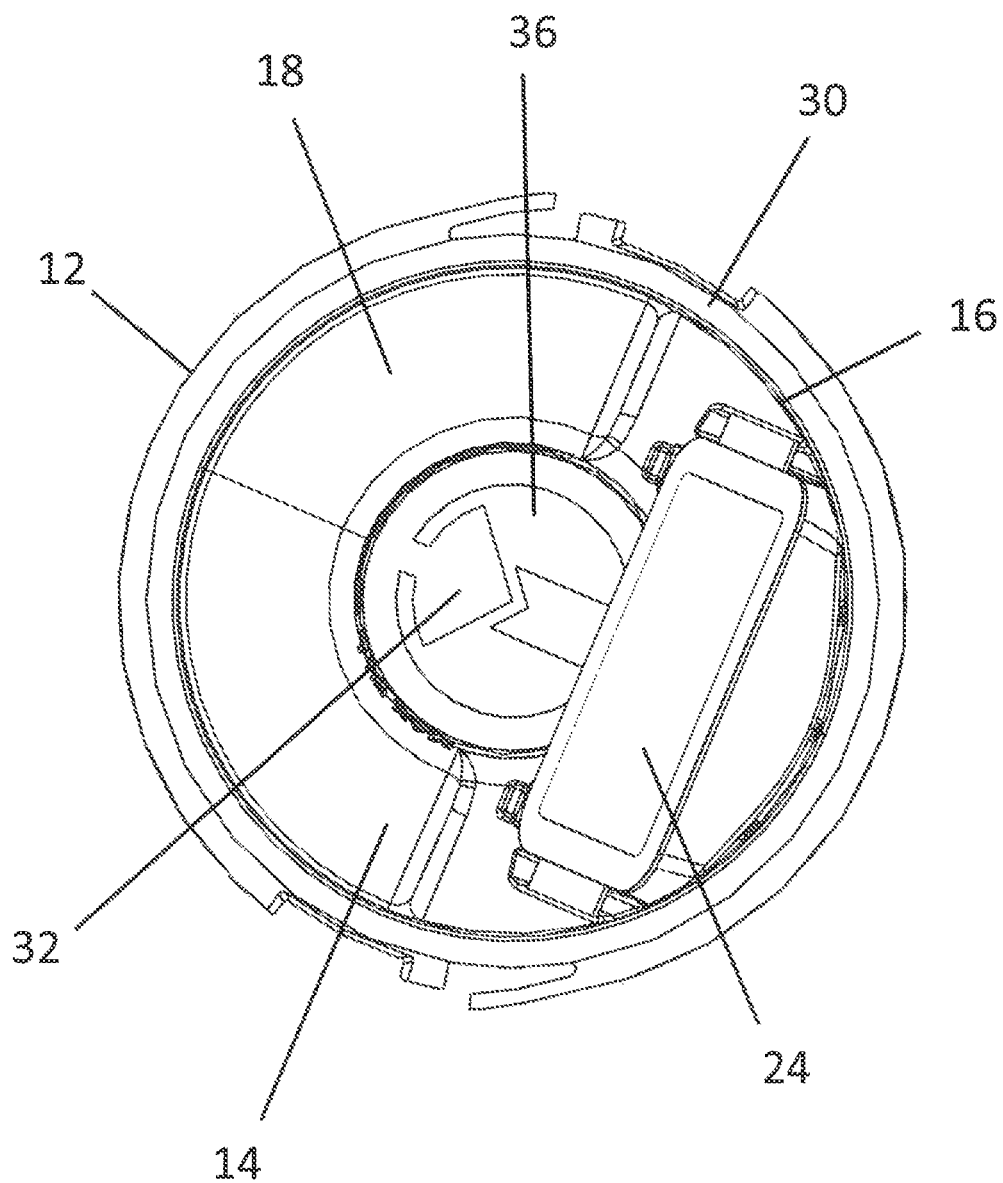
FIG. 8 shows a birds-eye view of the invention without the cap attached.
Figure 9:
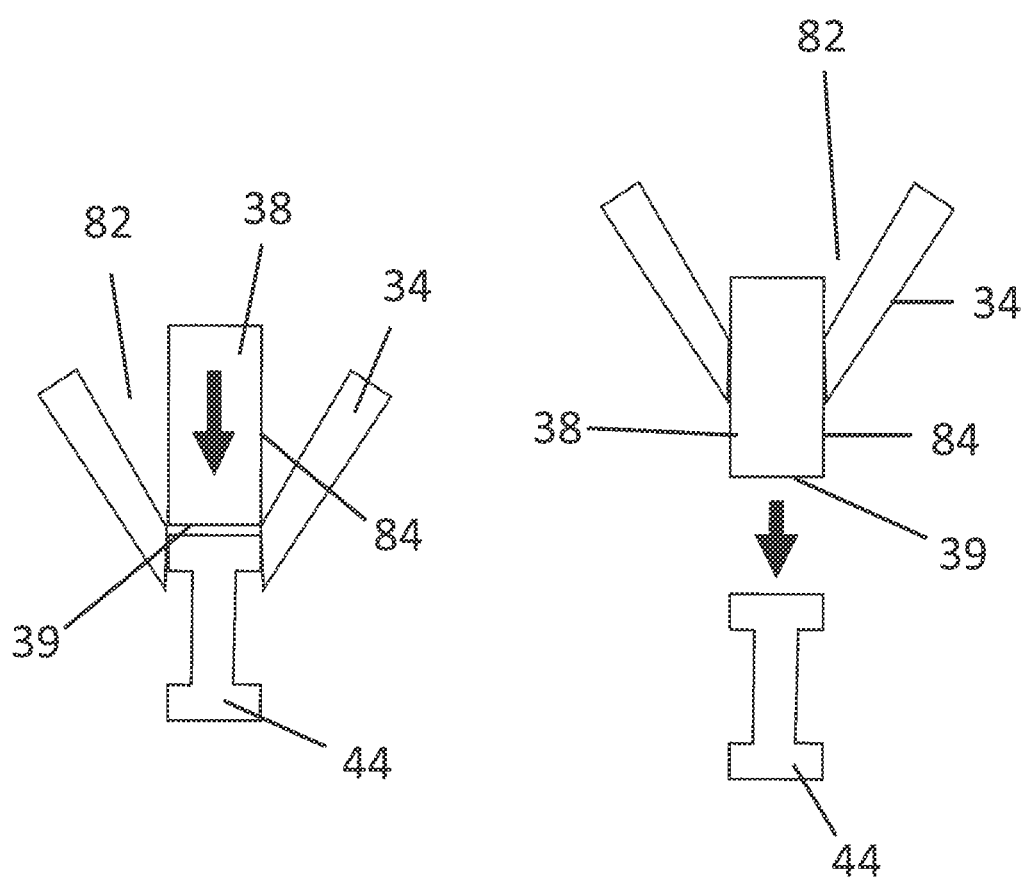
FIG. 9 shows a diagrammatic view of the plunger connecting to the magnet.

Blister 24 sits within upper compartment 14 as shown in FIGS. 1, 2 and 6. Blister 24 can be comprised of any suitable material known in the art. In use, the opening of blister 24 allows the sample to be mixed together with diluent 26 stored within blister 24 and with capture particles 28 with means of capturing target compound. Together, the entire mixed substance (mixture 1) flows down to the base of upper compartment 14, in use, due to gravity, when the device is in the upright position. In an embodiment, this movement of mixture 1 to the base of upper compartment 14 causes mixture 1 to submerge and come into contact with pelleted substance 43, optionally a lyophilised pellet, situated in nest compartment 40 directly below plunger 38 within cap 22, when the plunger is in the first, un-plunged position. In a preferred embodiment, pelleted substance 43 is a positive control in the form of a bacterial phage. When cap 22 is secured to cup 12, pelleted substance 43 within nest compartment 40 rests just above the base of upper compartment 14. Pelleted substance 43 will be mixed with mixture 1 to form mixture 2. When pelleted substance is a lyophilised pellet, this will be dissolved by mixture 1.

At this point, in a preferred method of use, the collection device 10 can be motioned in a swirling motion manually by the user or in an automated shaking, swirling or other appropriate motion device, to facilitate the dissolving of pelleted substance 43 to create mixture 2 whereby capture particles 28 with a means of capturing virus, capture the pelleted positive control bacterial phage as well as any virus within the sample. Mixture 2 includes capture particles 28, having captured the positive control bacterial phage as well as any target compound within the sample.

Figure 26:
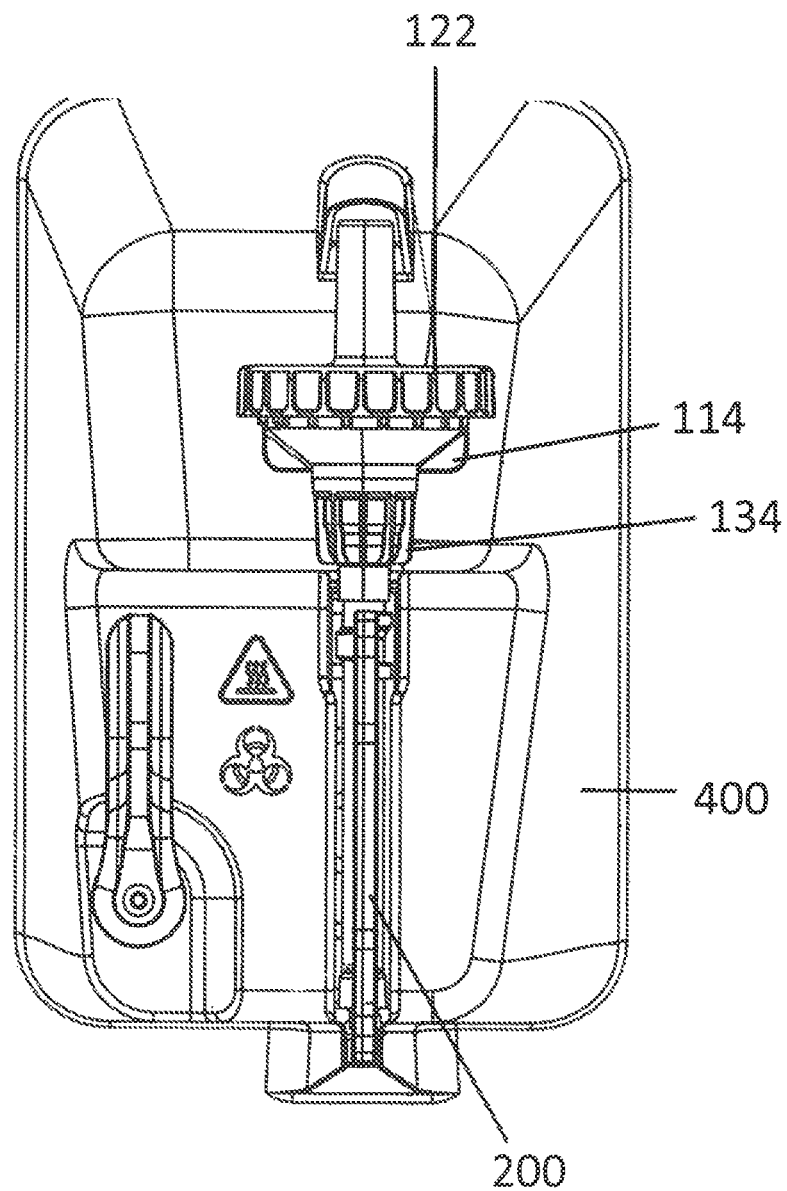
FIG. 26 shows a front view configuration of the invention assembled and inserted into a processing device.
Figure 27:
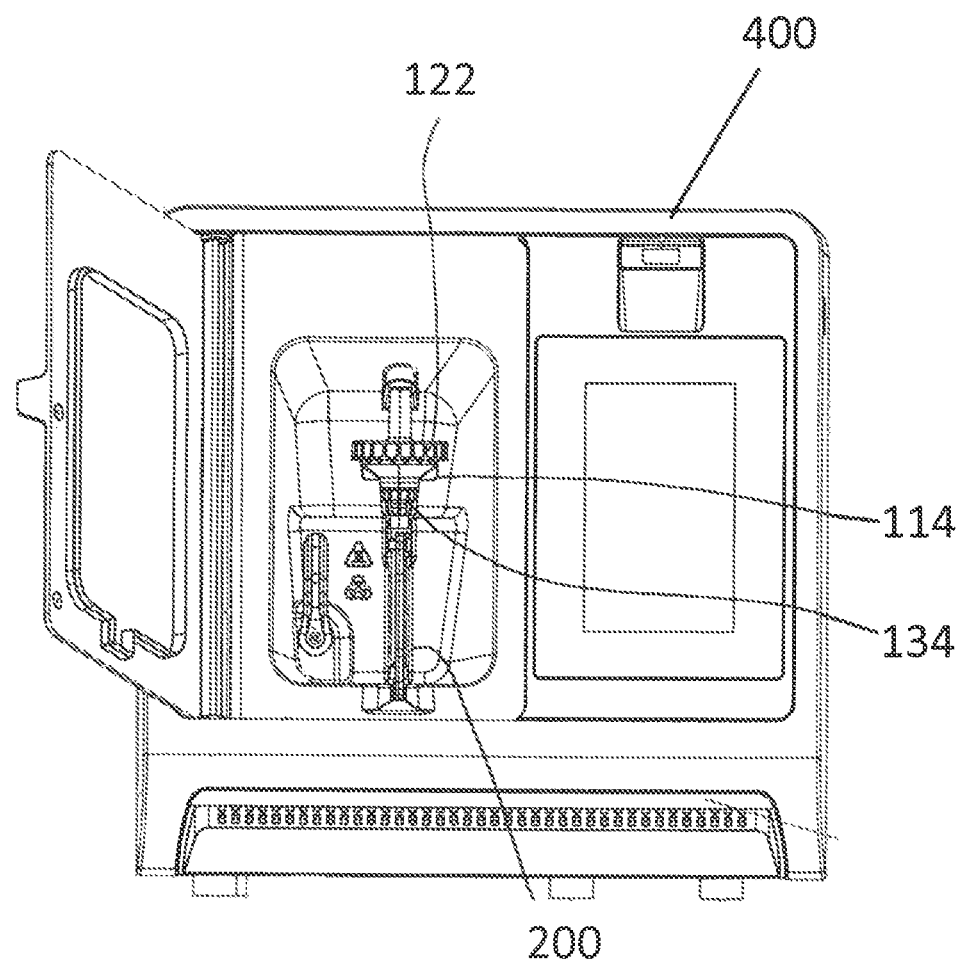
FIG. 27 shows a perspective front view configuration of the invention assembled and inserted into a processing device.

After the appropriate length of time and with the appropriate motion to allow for adequate mixing, mixture 2 sits directly below the base face of plunger 38 and directly above seal base 32 comprised of flaps 36 which divides upper compartment 14 from the lower compartment 34. Collection device 10 is manually connected to a detection cartridge 200 and the entire assembly 111 is inserted into detection control device 400 (FIGS. 26, 27). Plunger 38 is first activated by the detection control device. In a preferred embodiment of use, plunger 38, hidden within the mechanism of cap 22 is actuated by an instrument (not shown) for a determined amount of time after the twisting closure action of cap 22, allowing adequate time for the mixing of the diluent 26 stored in blister 24, with the sample and the compounds stored within nest compartment 40 at the base of upper compartment 14.

In a preferred embodiment, the plunger mechanism is activated by an instrument (not shown) within detection control device 400, which actuates a rod, pushing the plunger 38 in a downward motion through its internal tunnel, from a first unplunged position, into an initial plunged position into the upper compartment 14, until connecting with seal base 32 comprising flaps 36. Base 39 of plunger 38 comprises a flat surface that can connect with the magnet upper face. Flaps 36 facilitate the base 39 of plunger 38 in breaking though seal 32, by providing a sharpened edge to pierce seal base 32 as described below. Plunger 38 can be activated in two stages with a pause of sufficient, variable time to allow any required substance reactions to occur. In a preferred embodiment, the first plunger movement from a first unplunged position to an initial plunged position, is actuated after 30-60 seconds to allow adequate initial mixing for mixture 1 and for any positive control and for target compound capture to occur to create mixture 2. In a first stage, plunger 38 is moved sufficiently to an initial plunged position to connect with flaps 36 which comprise a sharp edge. The sharp edges may act to tear open seal base 32, at the base of upper compartment 14, causing mixture 2 to move into lower compartment 34 of cup 12 where magnet 44 is housed, optionally within magnet cage 42.

In use, after seal base 32 is opened, plunger 38 motion can be paused at this stage, stopping just above the surface of magnet 44 to allow adequate time for capture particles 28 with a means of capturing viruses or other biological target compounds within the sample, to reach magnet 44. Magnet 44 sits within lower compartment 34, optionally within magnet cage 42.

In the second stage of its action, from an initial plunged position to a further plunged position, plunger 38 pushes down further along an interior of cup 12, connecting with the top of magnet 44 or optionally magnet cage 42 housing it. In the further plunged position, the plunger 38 pushes magnet 44 and optionally magnet cage 42 down through to the bottom narrowest tapered opening 82. In being pushed downwards, magnet 44 drops through, into connected attachment tube 48 below, after passing through wiping means 50 contained within the bottom of the opening to ensure no saliva is brought through with magnet 44. Wiping means 50 captures any excess sample and acts to wipe down magnet 44 or magnet cage 42 before it enters attachment tube 48. The magnet or magnet cage entering attachment tube will act to introduce any attached capture particles into the attachment tube 48 for subsequent nucleic acid extraction.

In the further plunged position, base 39 of plunger 38 remains in narrow opening 82. Outer rim 84 around the circumference of base 39 of plunger 38 acts to seal lower compartment 34 of cup 12 from attachment tube 48 below, as exemplified in FIG. 9. This creates an air-tight, liquid-tight seal required for the subsequent extraction to work successfully. Magnet 44, magnet cage 42 and means of capturing virus 28 are therefore transported through, whilst any saliva sample is retained within cup 12.

In one embodiment, attachment tube 48 can be an extraction tube such as the PDQex tube manufactured by MicroGEM or to MicroGEM standards and as described in U.S. Pat. No. 10,758,900 or WO16144192 A1 hereby incorporated by reference into this application. In a preferred embodiment, the bottom of cup 12 is connected to a top of the extraction tube at the manufacturing stage via a Luer taper interface with protruding lines and is supplied pre-assembled. The PDQex extraction tube comprises a heat-deformable material, such that an inner chamber, into which the capture particles 28 with the captured virus is deposited, can, when heated, adopt a second configuration having a chamber volume less than the chamber volume of a first configuration, thereby expelling at least a part of the processed sample through a second opening from the device, optionally into a microfluidic cartridge.

In an alternative embodiment, pelleted substance 43, preferably a lyophilised positive control pellet, is stored to the side of plunger 38 rather than at the base of the upper compartment 14. In this embodiment, capture particles 28 can be mixed with the sample and positive control pellet by a twist mechanism of cap 22. Subsequent actions include a user sliding the entire attachment tube 48 into the detection cartridge device for analysis.

It is an intent of the invention that collection device 10 is used to efficiently collect a saliva sample, enrich the saliva sample by capturing any target compound and be used with a connectable attachment tube 48 to extract nucleic acid from any captured target compound for subsequent analysis and testing within a portable testing device which may provide results of the analysis, all within a rapid time frame, suitable for use in any field setting outside of the lab. The entire process may be carried out in one setting, by non-medical professionals in a time frame which is drastically shorter than the current laboratory sample collection, testing and analysis process.

Figure 10:
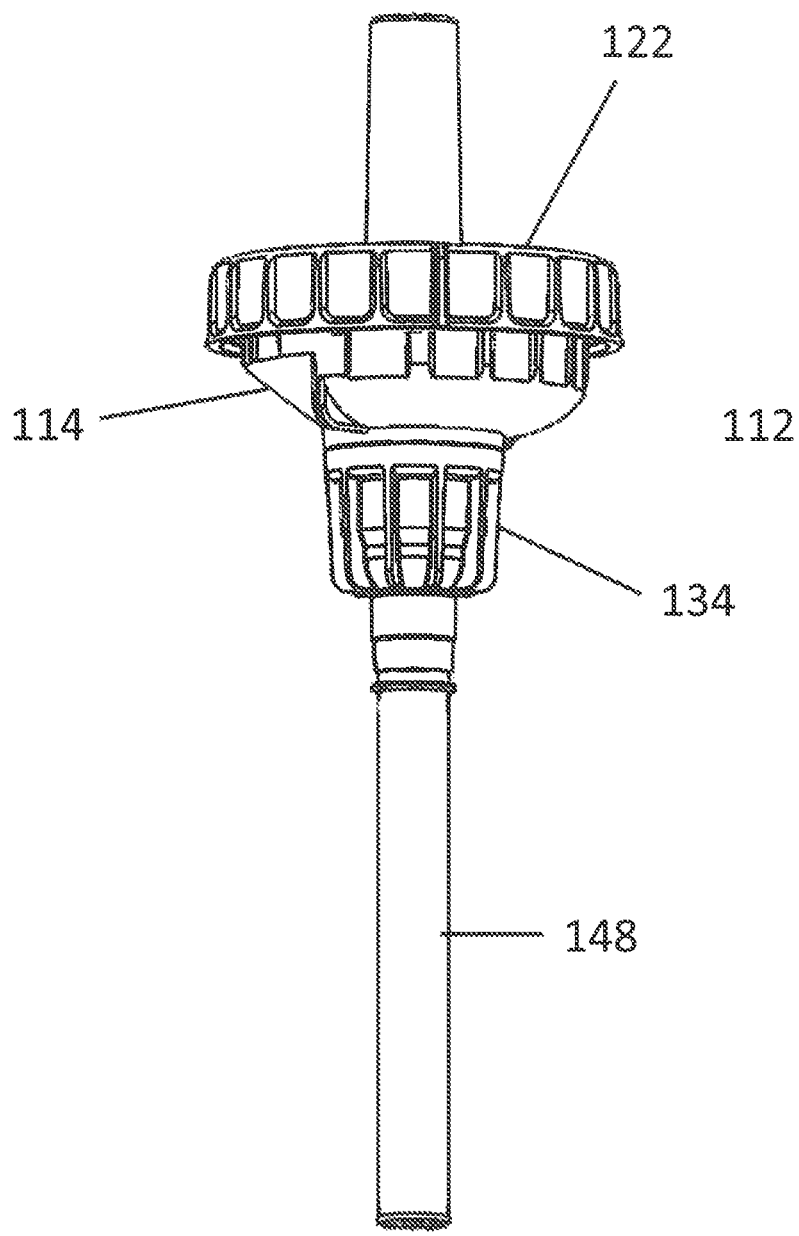
FIG. 10 shows a side view of an embodiment of the invention.

FIGS. 10-15 illustrate an alternative but similar functioning embodiment of the present invention. Cup 112 comprises tapered upper compartment 114 with extending walls 118 into which a sample is collected, such as a saliva sample from a patient. Upper compartment 114 can include blister 124 filled with diluent or similar solution 126 and optionally capture particles. Upper portion 130 of walls 118 of upper compartment 114 are capable of connecting to cap 122. In this embodiment, upper compartment 114 is not physically separated from lower, tapered compartment 134 and therefore collected saliva or other sample is able to flow down to the base of lower compartment 134 of cup 112. Lower compartment 134 of cup 112 can further comprise magnet 144, magnet cage 142 and guiding feature 115. FIG. 10 shows an exterior side view of cup 112 and a connected attachment tube 148. The outer exterior of guiding feature 115 can be viewed through the walls 134 of the lower compartment. Guiding feature 115 can act as a sample fill line guide for the user. In some embodiments guiding feature 115 can be coloured conspicuously so as to clearly been seen through the walls 134 of cup 112. Guiding feature 115 can simultaneously act as an internal guide to ensure the plunger 138 meets magnet 144 in the correct alignment and keeps magnet 144 positioned securely in transit.

Figure 14:
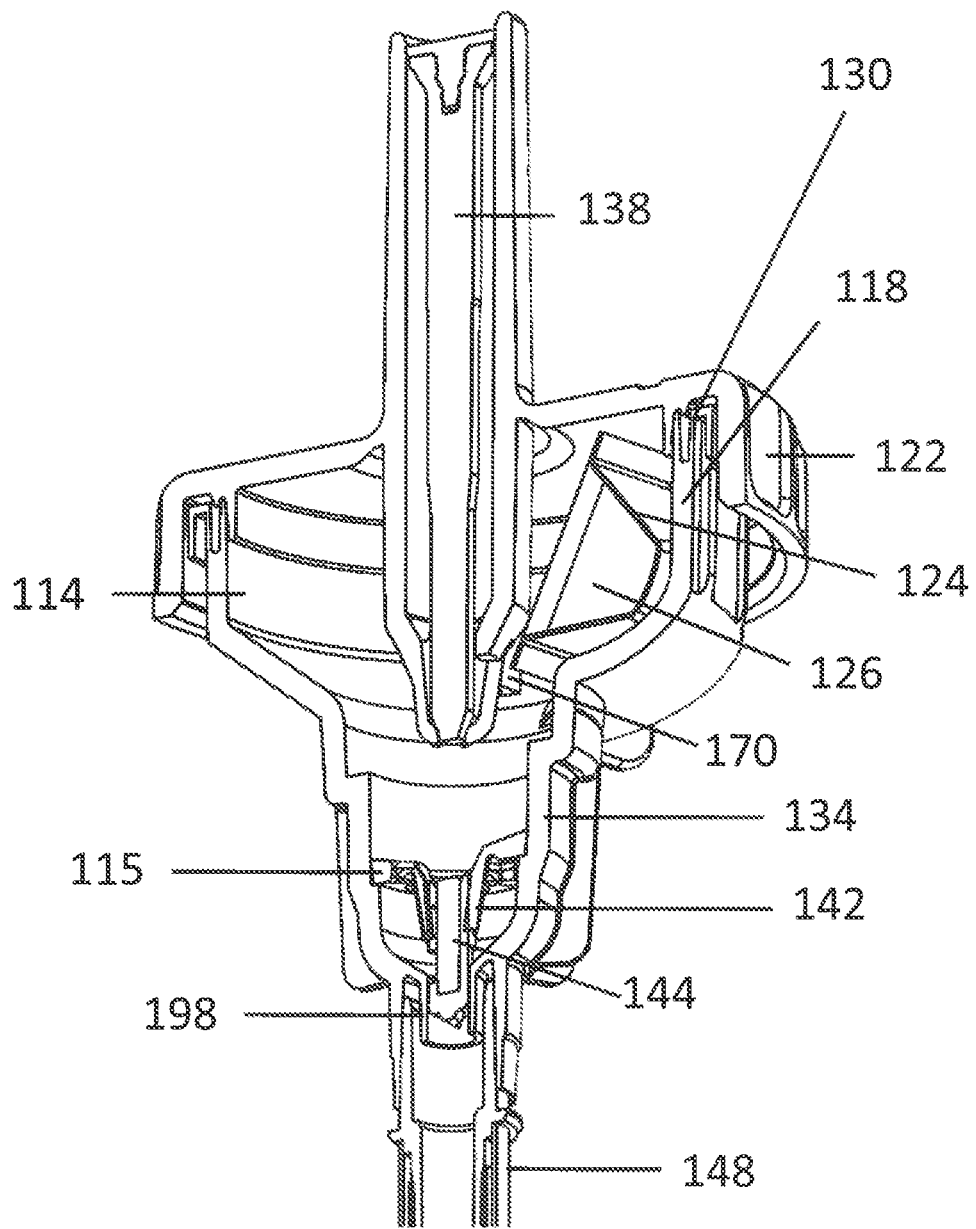
FIG. 14 shows a cross-section perspective view of an embodiment of the invention.
Figure 15:
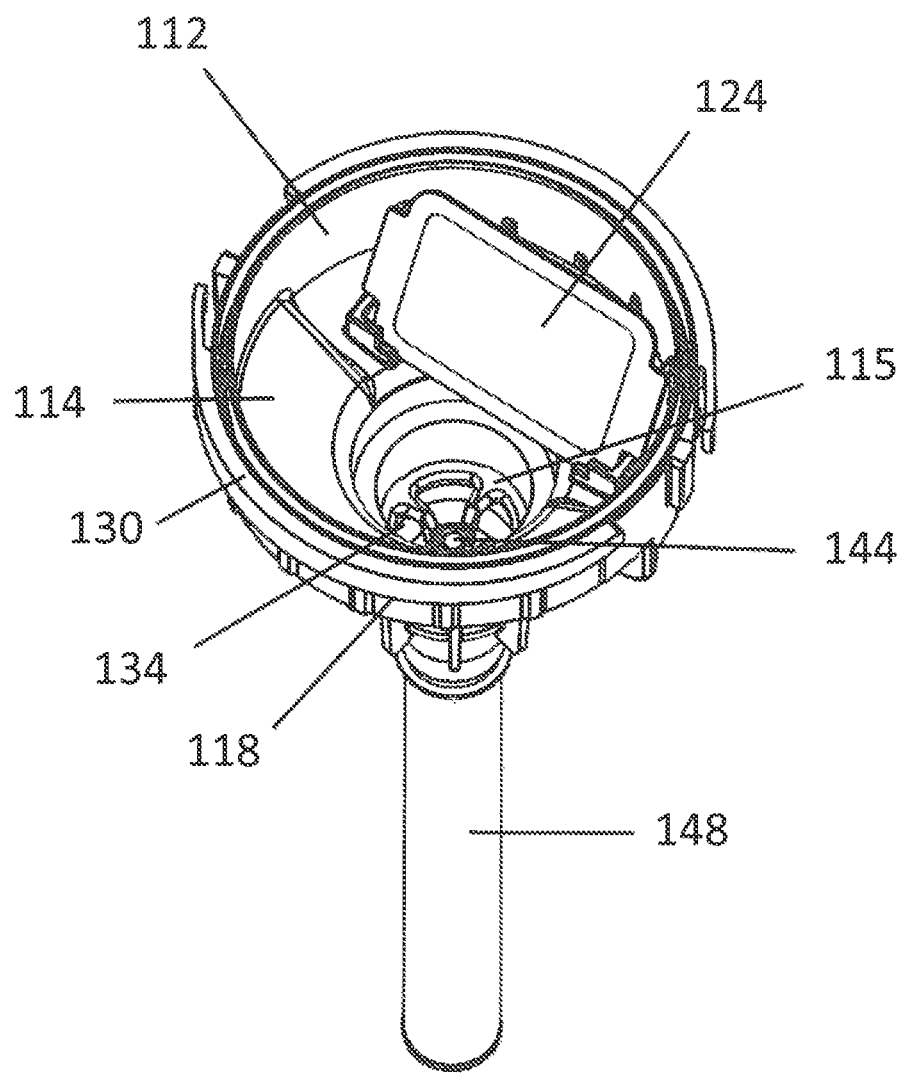
FIG. 15 shows a perspective view of an embodiment of the invention.
Figure 16A:
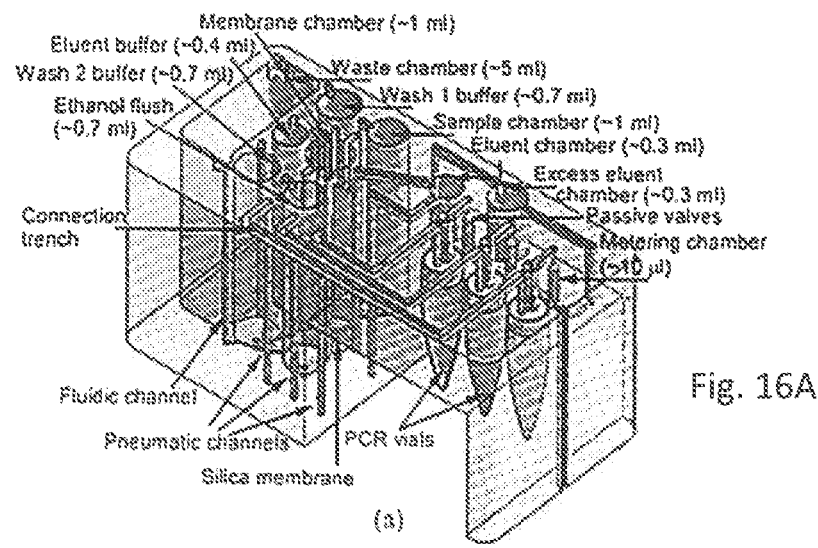
FIGS. 16A-16B are schematic diagrams of a prior art device.
Figure 16:
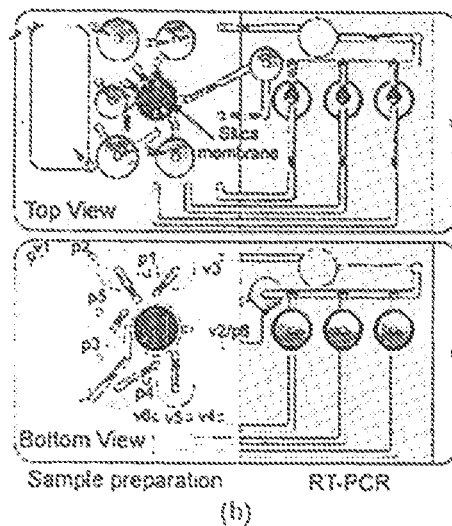

FIG. 14 shows an internal cutaway view of cup 112 with cap 122 connected. Lower compartment 134 can be seen, comprising magnet 144 and magnet cage 142 held within guiding feature 115. Magnet 144 can be a diametrically-poled magnet. Preferably, magnet 144 is moveably positioned within magnet cage 142 to allow for downward movement actuated by motion of plunger 138, similarly to the embodiment shown in FIGS. 1-9. In a preferred embodiment of use, magnet 144 will attract magnetic capture particles from the sample, having captured any target compound. These capture particles will stay connected by magnetic attraction to magnet 144 allowing magnet 144 and capture particles to be moved into attached attachment tube 148. The downward movement of plunger 138 will act to push magnet cage 142 and magnet 144 down through into the attachment tube 148 where magnet 144 and magnet cage 142 will fall freely within the attachment tube 148. This action will take place after enough time has elapsed to allow sufficient attraction of magnetic beads to magnet 144.

Figure 11E:
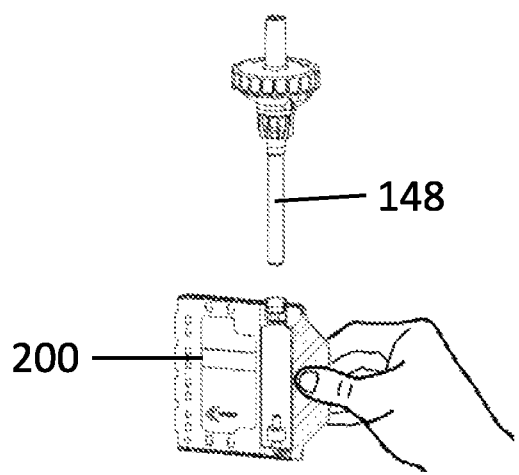
Figure 12:
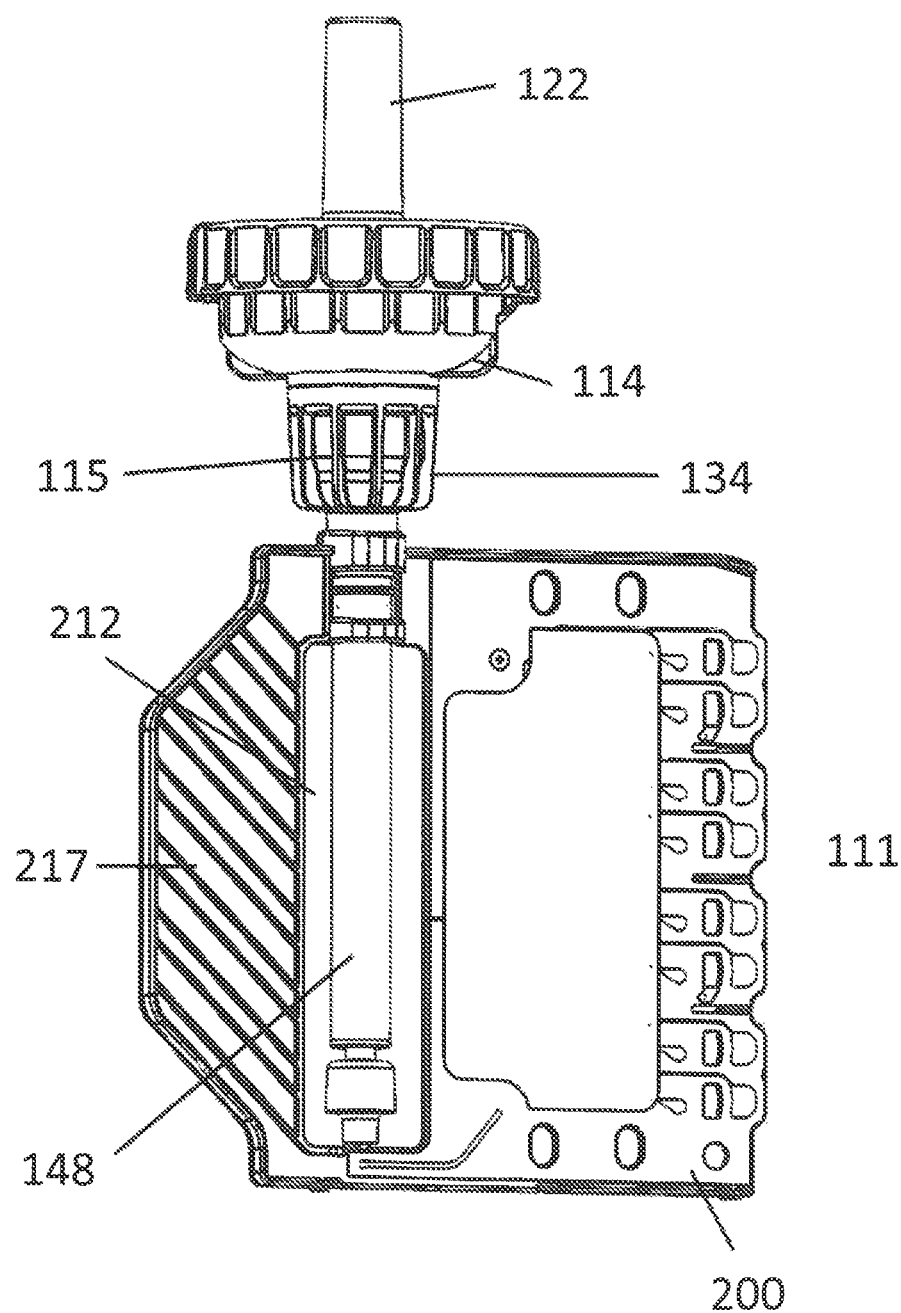
FIG. 12 shows a perspective view of an embodiment of the invention.
Figure 20:
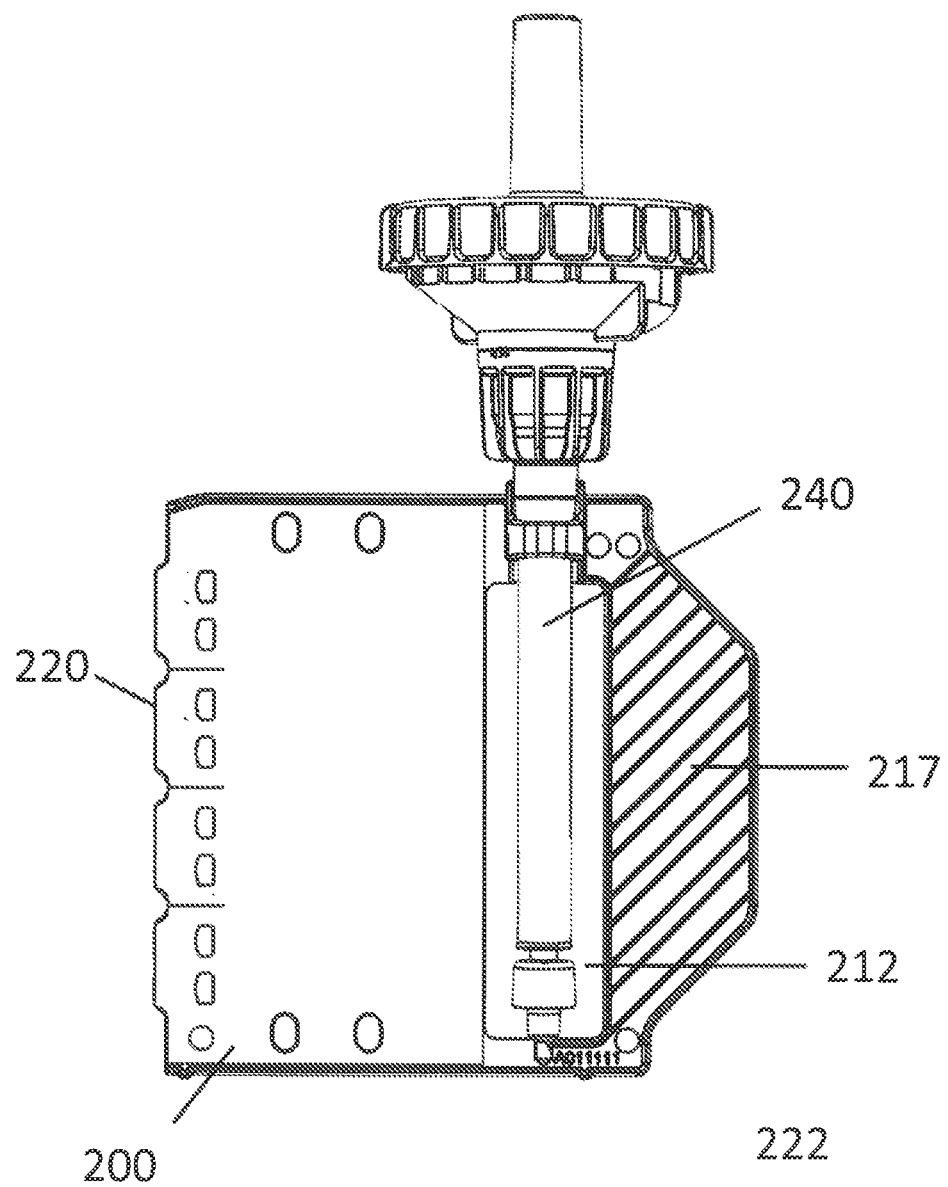
FIG. 20 shows an outline view of an assembled extraction tube within a cartridge opening of the microfluidic cartridge.
Figure 21:
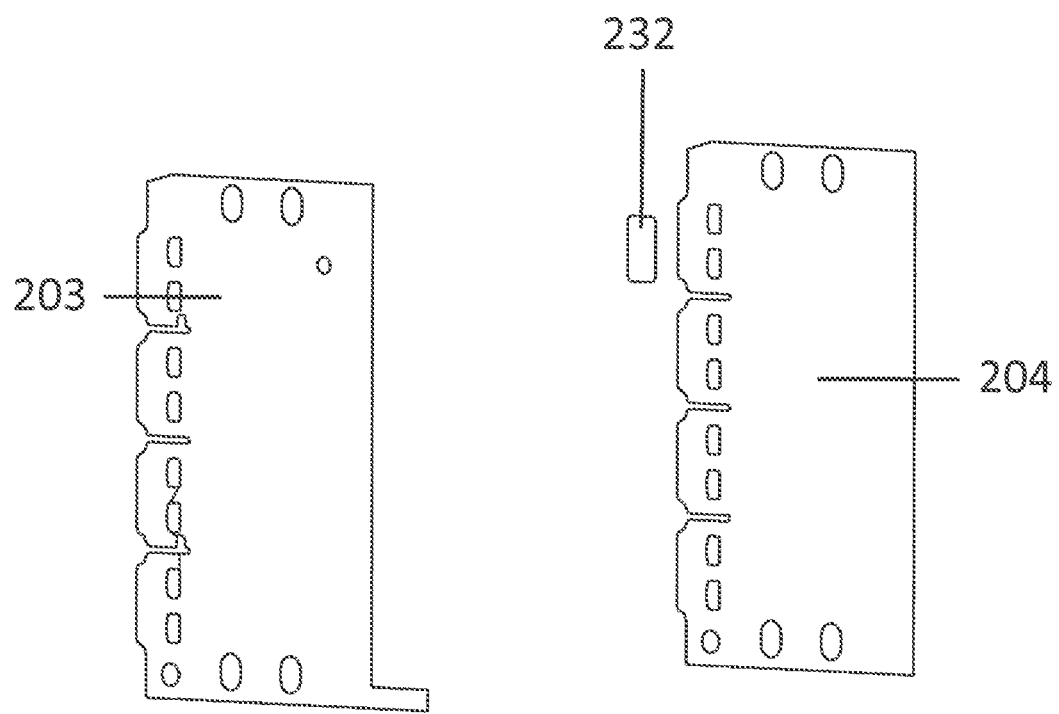
FIG. 21 shows a disassembled configuration of the microfluidic cartridge.

In an embodiment, the connection of the saliva cup 112 to a subsequent attachment tube 148 and microfluidic cartridge or other suitable testing cartridge 200, is completed during a manufacturing stage to provide a fully assembled device 111 as shown in FIG. 12 and assembled device 222 shown in FIG. 20. In an alternative embodiment cup 112 is provided unconnected but configured for subsequent attachment to an attachment tube 148. In a further alternative embodiment, cup 112 is pre-assembled to only extraction tube 148 for subsequent insertion into cartridge 200, as shown in FIG. 11E and FIG. 13.

Figure 11A:
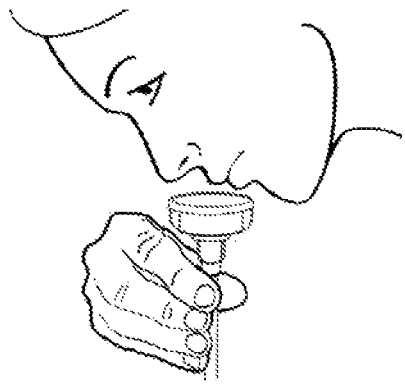
FIG. 11A-E show diagrammatic views demonstrating use of the invention.
Figure 11B:
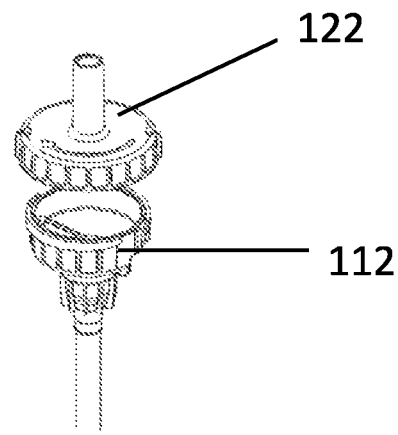
Figure 11C:
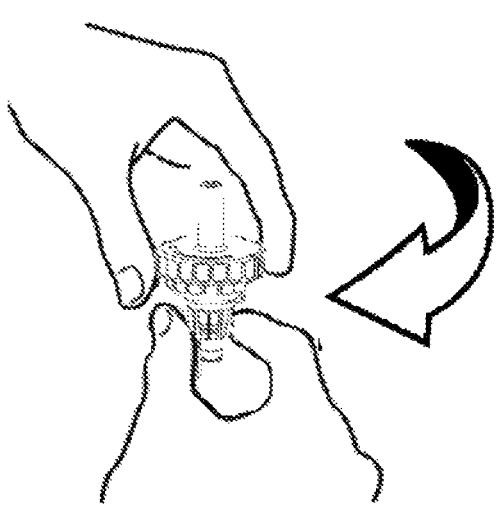

In use, after collection of saliva or other sample within upper compartment 114 as shown in FIG. 11A, cap 122 is closed and secured onto and over walls 118 of cup 112 as shown in FIG. 11B. Secure closure can be achieved by a twist mechanism to be actioned by the user, as shown in FIG. 11C.

Figure 13:
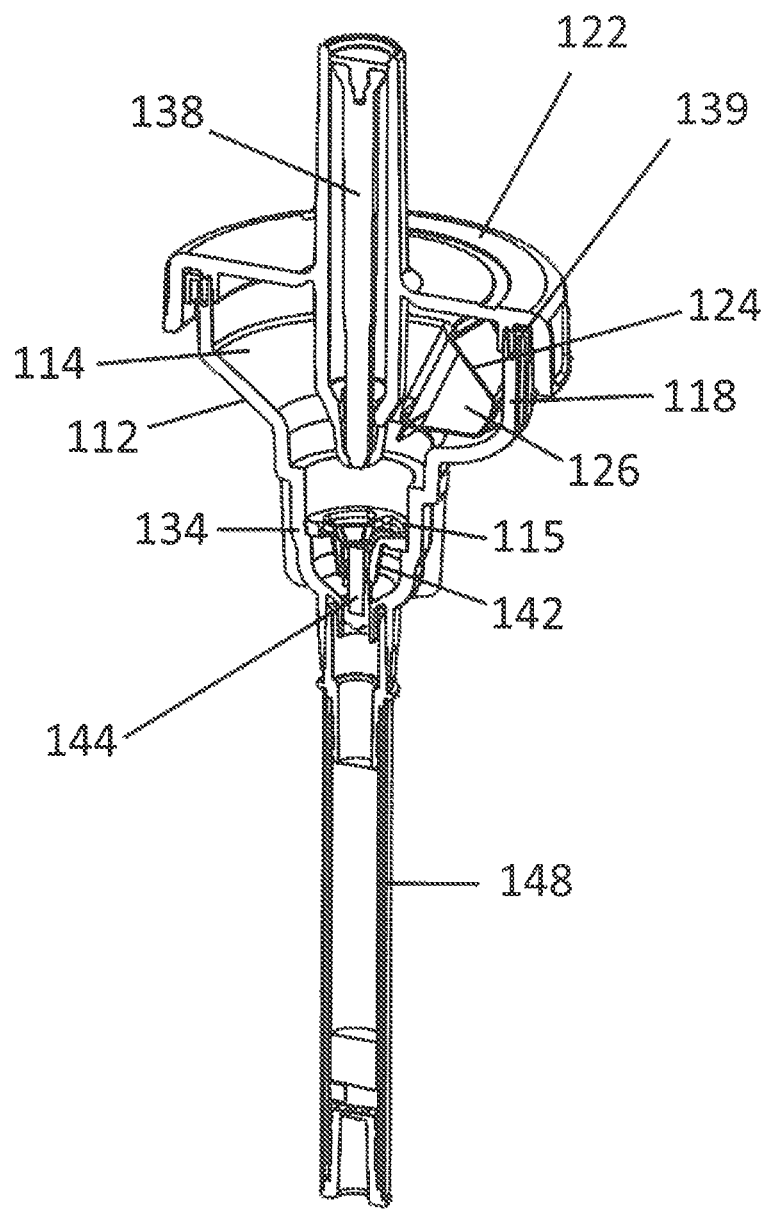
FIG. 13 shows a cross-section perspective view of an embodiment of the invention.

The user-actioned, twist closure mechanism brings piercing mechanism 170 shown located within the interior of cap 122, into contact with the surface of blister 124 filled with diluent 126 as shown in FIG. 13. This movement causes opening of blister 124 for example by piercing or tearing of a foil portion of blister 124 and triggering diluent 126 and capture particles within to empty out the blister compartment and mix with the collected saliva sample within cup 112. Once blister 124 is pierced open, the collected sample is mixed together with diluent 126 and means of capturing any pathogen or virus or other target compound to form an enhanced or enriched mixture. In one embodiment, the target compound is the virus is SARS-CoV-2 associated with the disease COVID-19.

Figure 11D:
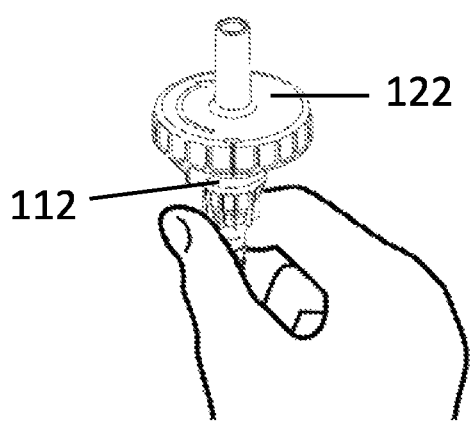

In use in this embodiment, no positive control is present within the nest compartment, and alternatively there is no nest compartment present within cup 112. In use, in this embodiment, a suitable positive control can instead be introduced downstream. The enriched mixture comprises the user's sample together with diluent 126 and magnetic capture particles. As shown in FIG. 11D, shaking or twisting, or swirling action by the user happens following the attachment of cap 122, to facilitate sample mixing with the diluent, compound capture, and attraction of magnetic beads to the magnet. In the present embodiment, this action can be taken for a certain time period between about 5-200 seconds or may not be required. Alternatively, cup 112 can be placed in a twisting or swirling mechanical device such as those typically found in a laboratory, to enable the appropriate motion to occur.

Following the action taken as shown in FIG. 11E to assemble cup 112 together with a suitable detection cartridge 200, forming assembled device 111, the magnetic capture particles located within the enhanced mixture can be attracted towards magnet 144. In this embodiment, the entire assembled device 111 can be inserted into a detection control device (FIGS. 26 and 27) which can control the plunger action, required heating controls, amplification, detection and analysis.

Similarly to the previous embodiment, the detection/control device (exemplified in FIGS. 26 and 27) may actuate a rod (not shown), causing the plunger 138 to be pushed in a downward motion, through its internal tunnel within cap 122, from a first unplunged position, into a first plunged position sufficiently to connect with the top of magnet 144 or optionally magnet cage 142 housing it. Guiding feature 115 can act to guide the plunger to align accurately with the top of the magnet. This subsequent movement of plunger 138 from the first plunged position to a further plunged position acts to push magnet 144 and magnet cage 142 down through to the bottom narrowest tapered opening and into an extraction tube 148 or suitable attachment tube for collection or further processing.

Outer rim portion 198 may be included around the outer circumference of the magnet cage 142 to retain the sample within cup 112 as shown in FIG. 14.

Preferably attachment tube 148 is an extraction tube. In one embodiment, extraction tube 148 can be a PDQex tube manufactured by MicroGEM or to MicroGEM specification or alternative suitable lysis tube. The PDQex comprising a heat-deformable material and functions as previously described. Suitable extraction reagent can be included within the extraction tube. These reagents can be thermostable enzymes such as those refenced in U.S. Ser. No. 10/758,900, this patent is hereby incorporated by reference in its entirety into this application. In a preferred embodiment, the bottom of cup 112 is connected to the top of the PDQeX extraction tube at the manufacturing stage via a Luer taper interface with protruding lines.

In an alternative embodiment, the sample to be collected may include other bodily fluids and tissue including but not limited to blood, urine, skin cells, mucus, plasma and serum, faecal matter, cultured cells, vaginal fluid, semen or sputum as well as plant tissue, microorganisms, water or soil or, edible fluids such as beverages and anything that might be needed to test for the presence of a certain target compound or nucleic acid. The fill line, perimeter size and shape can be adjusted to suit the sample requirement.

In further alternative embodiments of the invention, the diluent blister is stored in a compartment within the cap or is directly beneath the plunger, whereby the closing mechanism of the lid causes the bursting of the blister due to pressure to releases the diluent or other substance. The blister may be formed of a laminate pouch with a heat seared rim to be squeezed open by pressure from the cap closure mechanism or any material suitable for tearing, ripping or squeezing open with the action of the lid. The diluent blister may be held in place via a compartment or holding means.

In further alternative embodiments the nest compartment, below the plunger, within the cap may house various suitable compounds to be mixed with the collected sample. This compound can be in the form of a lyophilised pellet or others suitably enriched or modified compounds for enriching the sample.

In a further alternative embodiment, the magnet or magnet cage is attached to the base of the plunger and is brought down into the cup with the lowering action of the plunger from the first un-plunged position to the initial and further plunged positions. The magnetic capture particles will be attracted to the magnet in the same way after having been mixed with the sample. A second stage of action of the plunger can then push the magnet down into the attachment tube 148. A barrier layer can be situated beneath magnet cage 142 to prevent the magnet entry into attachment tube 148 prematurely. The barrier layer can comprise foil or suitable material, which can be broken through when the magnet or magnet cage gets pushed by the plunger, into the attachment tube. The barrier layer can serve the purpose of sealing any required substances such as but not limited to reagents and buffer, within the attachment tube 148.

In an alternative embodiment, the wipers at the base of the cup can be any suitable material capable of removing the sample from the magnet or magnet cage or may not be a necessary requirement depending on the sample collected. Suitable materials include but are not limited to bristles, rubber wipers and/or felt strip surrounding the outer rim of the exit opening and acting to prevent unnecessary sample entering the attachment tube.

In a further optional embodiment, the plunger may be activated by the user or device handler for example where the user is a medically trained professional with instructions provided on the required time delay with first and second plunging actions.

Optional means for achieving adequate mixing of the capture particles with the sample in a suitable amount of time may include: written, visual or audible instructions for the user to motion the cup for a required amount of time; adding a chemical agent to cause effervescence within the sample included but not limited to effervescent tablet formations.

Further examples of use include collection of multiple users' samples within one cup. This pooling of samples can be done by users depositing as mentioned previously, individual saliva sample into the same cup in succession. Alternatively, additional saliva collecting tubes can be used to individually transfer a saliva sample from a user to the single cup. The cup can be varied in size to accommodate multiple sample types and quantities of sample. The device will work essentially in the same way as previously described for pooling of samples. A separate device can be used to transfer multiple individual samples to the cup compartment. The separate device can be configured to securely interact with the cup compartment.

In certain embodiments, the cup can be configured to fit, communicate or interact with additional devices including but not limited to: devices to facilitate and/or automate saliva collection and discharge into the cup including mouthpieces, swabs and saliva production catalysts, features to indicate adequate sample collection including built-in measurements and sensors, features to facilitate sample collection including holders, features to divide the sample into separate portions including separate chambers within the compartments, features to amend the shape or diameter of the cup to allow communication with varying sized upstream processing devices.

In further alternative embodiments, the attachment tube is a vessel for storage, visual analysis, further enrichment, purification or other suitable downstream processing.

Figure 17:
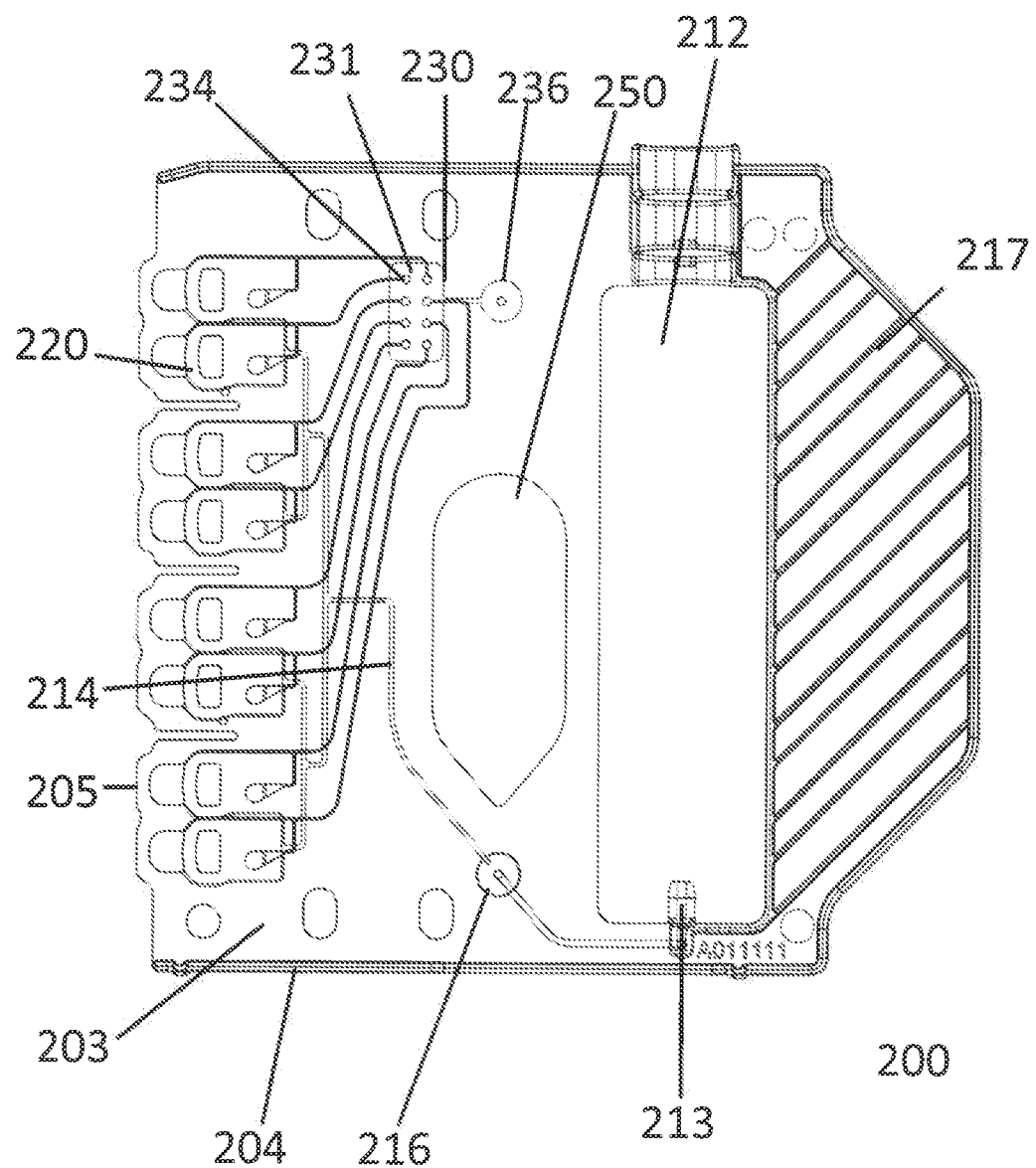
FIG. 17 is a schematic diagram of a microfluidic cartridge in accordance with the teachings of the present invention.
Figure 23:
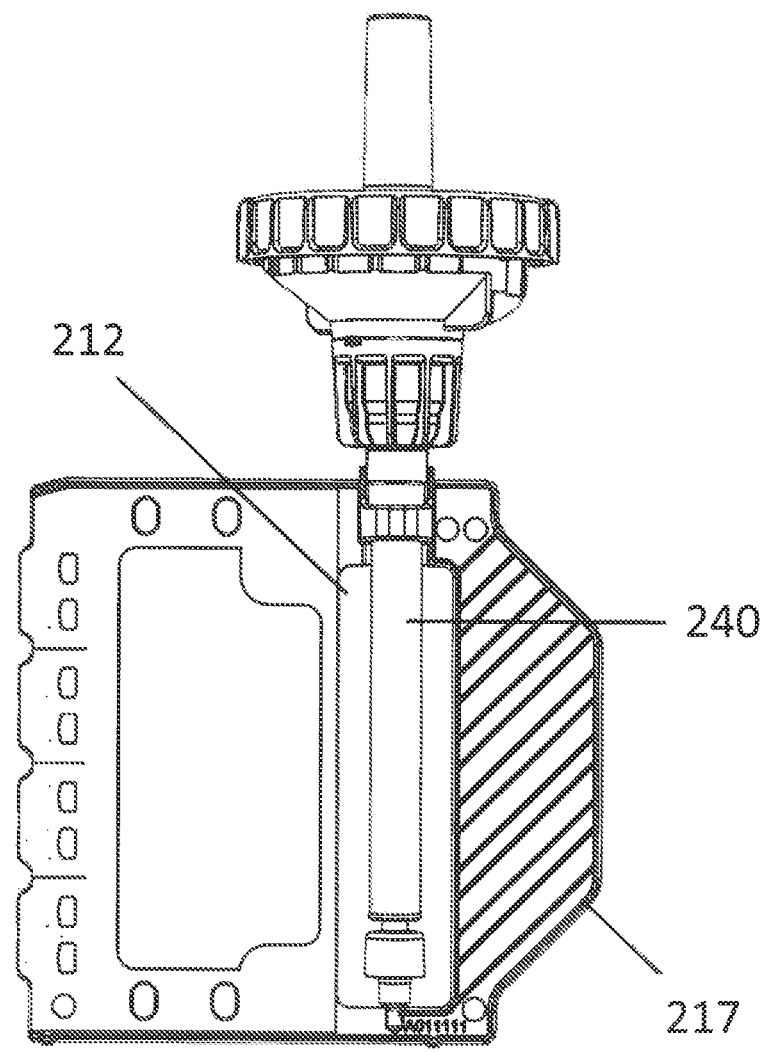
FIG. 23 shows an of the microfluidic cartridge including a gripping area.

FIG. 17 shows microfluidic cartridge 200 configured for connection to extraction tube 240 (FIGS. 20, 23). In a preferred embodiment, extraction tube 240 is configured to provide a sample to be amplified via a polymerase chain reaction (PCR) within microfluidic cartridge 200 and analyzed via subsequent detection and analysis processes such as a detection laser and fluorometer. Microfluidic cartridge 200 is configured with cartridge opening 212 for insertion of extraction tube 240 by a user or insertion during a manufacturing assembly phase to be provided to a user pre-assembled. FIG. 20 shows assembled extraction tube 240 within cartridge opening 212. Cartridge opening 212 for extraction lies vertically within the same plane as microfluidic cartridge 200. The plane can be horizontal.

Microfluidic cartridge 200 is configured for insertion into control detection device 400, as shown in FIGS. 26 and 27.

Microfluidic cartridge 200 comprises a planar surface with two faces 203, 204 and outer front edge 205. A network of microfluidic channels 214 connects extraction tube 240 to a plurality of chambers 220 for amplification. The plurality of chambers 220 are stacked vertically within the planar surface of microfluidic cartridge 200. Optionally, chambers 220 can be stacked horizontally or diagonally. In a preferred embodiment, the amplification for which the cartridge is configured, is a polymerase chain reaction (PCR). In a preferred embodiment, there are eight separate chambers 220 used for PCR. In use, each of the plurality of chambers 220 comprise fillable area 224 which is pre-loaded with necessary PCR reagents. In a preferred embodiment, the pre-loaded amplification reagents may include a Mastermix, enzymes, primers and probes including nucleotides for the amplification of nucleic acid from a sample.

Cartridge opening 212 is configured within microfluidic cartridge 200 to allow for insertion of extraction tube 240 which can contain pre-filled reagents to prepare a sample to be analyzed. Connection interface 213 situated at the lower end of opening 212, provides a connection to extraction tube 240. In a preferred embodiment, connection interface 213 is a barb fitting. Alternatively, connection interface 213 can be any adequate connection to provide a standardized level of secure join of extraction tube 240 including but not limited to a Luer taper fitting. Cartridge opening 212 is shaped to fit the entirety of tube 240. In a preferred embodiment, once the extraction tube 240 is inserted into cartridge opening 212 of cartridge 200, it is irremovably fixed in place. FIG. 20 shows the assembled configuration with extraction tube 240 inserted into microfluidic cartridge 200. Collection cup 112 can be attached to extraction tube 240 to be situated above the upper edge of microfluidic cartridge 200, within cartridge opening 212.

Area 217 of microfluidic cartridge 200 comprises a flat surface area where microfluidic cartridge 200 can be held or gripped by a user as shown in FIG. 23 for the required use including insertion into detection device 400 such as that shown in FIGS. 26 and 27. In a preferred embodiment, area 217 is configured for adequate grip by a user and may comprise a rough surface, ridges or another suitable surface.

The microfluidic channels 214 branch out into a tree structure each leading from connection interface 213 of extraction tube 240 to one of the plurality of chambers 220. Inlet valve 216 sits within microfluidic cartridge 200 close to the interface connection 213 between extraction tube 240 and microfluidic channel 214 for carrying the sample to the chambers 220. In use, inlet valve 216 prevents any back flow of the sample back into extraction tube 240. Inlet valve 216 can be ring-shaped and specifically, can be identical to subsequently mentioned ring-shaped valve 236. For the sake of clarity, "inlet valve" will be hereinafter be used to refer inlet valve 216 and "ring-shaped valve" to refer to ring-shaped valve 236.

Figure 19:
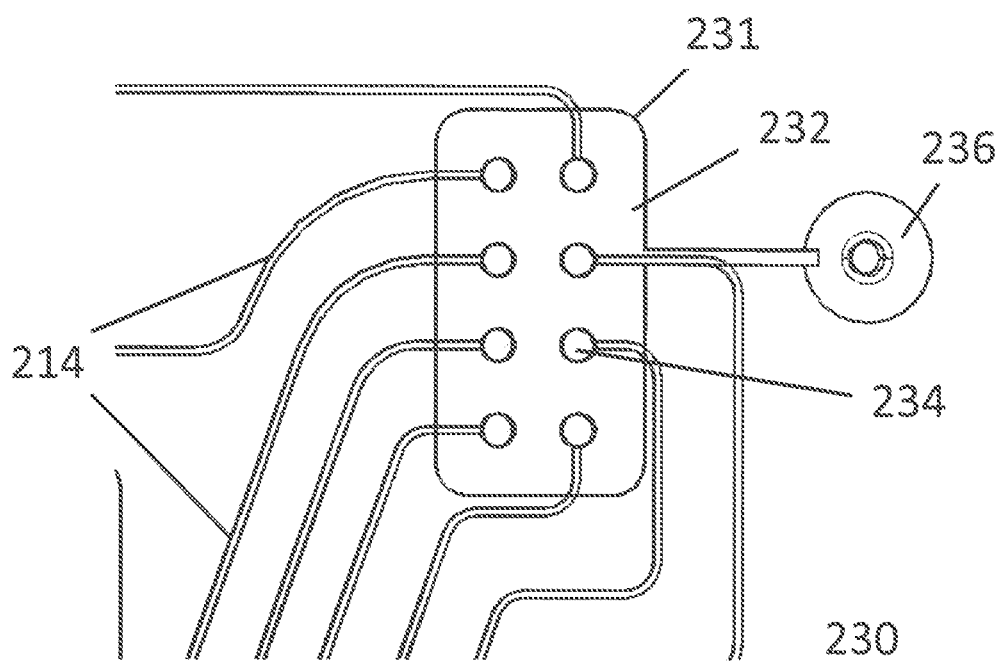
FIG. 19 is a schematic diagram of a hydrophobic valve for use with the microfluidic cartridge in accordance with the teachings of the present invention.

Microfluidic channels 214 separately lead away from each chamber 220 to hydrophobic junction valve 230 within microfluidic cartridge 200. In a preferred embodiment, hydrophobic junction valve 230 comprises junction 231 covered by a hydrophobic membrane 232. FIG. 19 shows a preferred embodiment of the structural arrangement of hydrophobic junction valve 230. In this arrangement, a plurality of individual units 234 within junction 231 are arranged, each unit 234 with further connection to ring-shaped valve 236. Ring-shaped valve 236 is not covered by hydrophobic membrane 232.

In a preferred embodiment, junction 231 comprises eight units 234 laid out in a rectangular two by four configuration. Each chamber 220 is fluidically connected to an individual unit 234 of junction 231.

In use, liquid will be pushed into channels 214 of the detection cartridge through connection interface 213 and through inlet valve 216. Inlet valve 216 is initially in the open position. Liquid will fill each of chambers 220 and will flow to fill individual valve units 234 within junction valve 231.

Hydrophobic membrane 232 lies above valve units 234. Liquid is unable to pass through hydrophobic membrane 232. Air may pass through the hydrophobic membrane where it will reach the ring-shaped valve 236 where it may escape to the atmosphere. When all eight individual valve units 234 are filled, ring-shaped valve 236 is closed.

FIG. 19 shows junction 231 of hydrophobic junction valve 230 in more detail. The closure of both the inlet-valve 216 and ring-shaped valve 236 can be controlled by device control system 400 which is exemplified in FIGS. 26 and 27.

In use, hydrophobic junction valve 230 is initially in a position open to the atmosphere. The control device 400 will action the closure of hydrophobic junction valve 230 once liquid has filled all eight units 234. When both the hydrophobic junction valve 230 and inlet valve 216 are closed, a sealed environment is created which can be a pressurized liquid environment, so the valves act to limit the amount of vapor that can build up within the sealed environment. The entire microfluidic cartridge 200 is coated in an adhesive film which seals the microfluidic channels 214.

Figure 18:
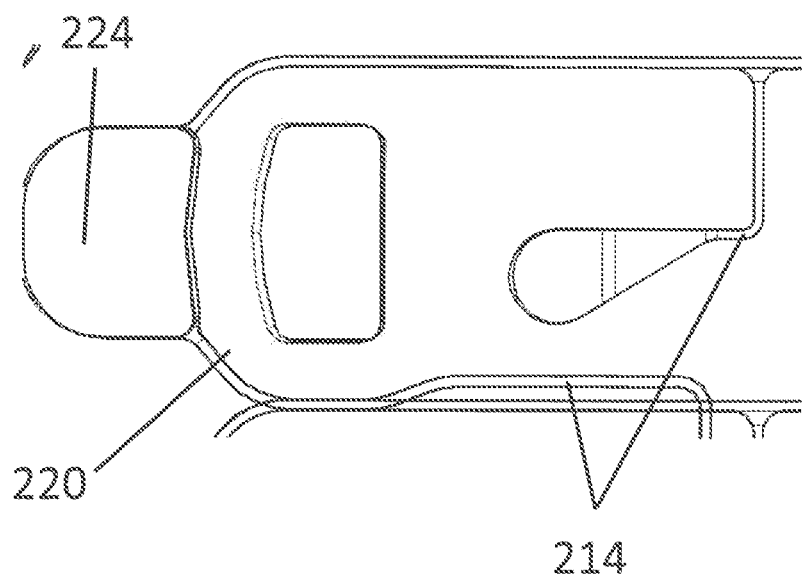
FIG. 18 is a schematic diagram of a single amplification chamber with a fillable unit.
Figure 22:
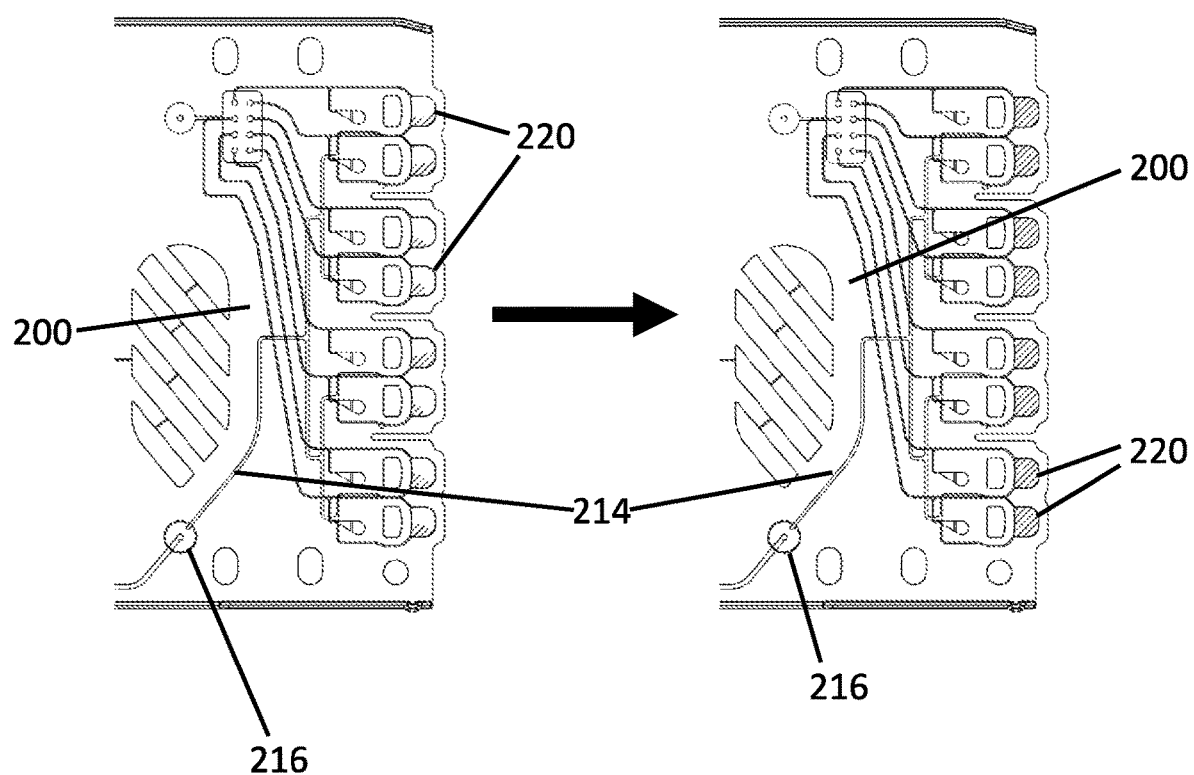
FIG. 22 shows filled chamber windows during use.

FIG. 18 shows an image of a single chamber 220 with fillable unit 224 where the sample will flow to and where PCR amplification occurs with the pre-filled reagents. The filled chamber windows 224 are shown in use in FIG. 22 where they can be seen partially and fully filled during a period of use. Chambers windows 224 are transparent to detect results.

Microfluidic cartridge 200 can comprise central aperture portion 250 configured to act as an area for mixing where necessary with additional reagents. In some embodiments the nucleic acid sample and PCR reagents can be prevented from mixing until reaching central mixing portion 250. In various embodiments, an additional device can be inserted within central portion 250 to facilitate mixing via an appropriate mechanism including but not limited to vibration or magnetic "on-chip" mixing.

In use, microfluidic cartridge 200 is inserted within a detection control device 400. Control device 400 can include heaters for thermocycling which can sit on both sides of microfluidic cartridge 200 to provide the necessary heating and cooling for PCR or alternative processing. A fluorometer within control device 400 can be used to detect fluorescence within chambers 220. In use, fluorescence detection can be done via the outer front edge 205 of microfluidic cartridge 200 or via the planar faces of the chambers 220.

Detection control device 400 can be operated by a user who is inexperienced in the amplification and detection processes involved, as the process is automated by the device control software programming. Suitable software coding can be used to program the detection device and automated hardware, including control of the valve closure and opening, thermocycling and sample preparation within the extraction tube. The detection control device 400 may comprise a suitable output interface and can be connected to central database via a wireless connection.

In a preferred embodiment, microfluidic cartridge 220 is a single-use cartridge designed to be removed from detection device 400 and disposed of after analysis in the device. Any suitable material is possible for the construction including plastic, polymeric material and glass. Disposal after use must be done in a biohazardous waste.

In use, the sample collection, nucleic acid extraction and amplification is completed within the device with no interference. The nucleic acid extracted is suitable for direct amplification.

Figure 24:
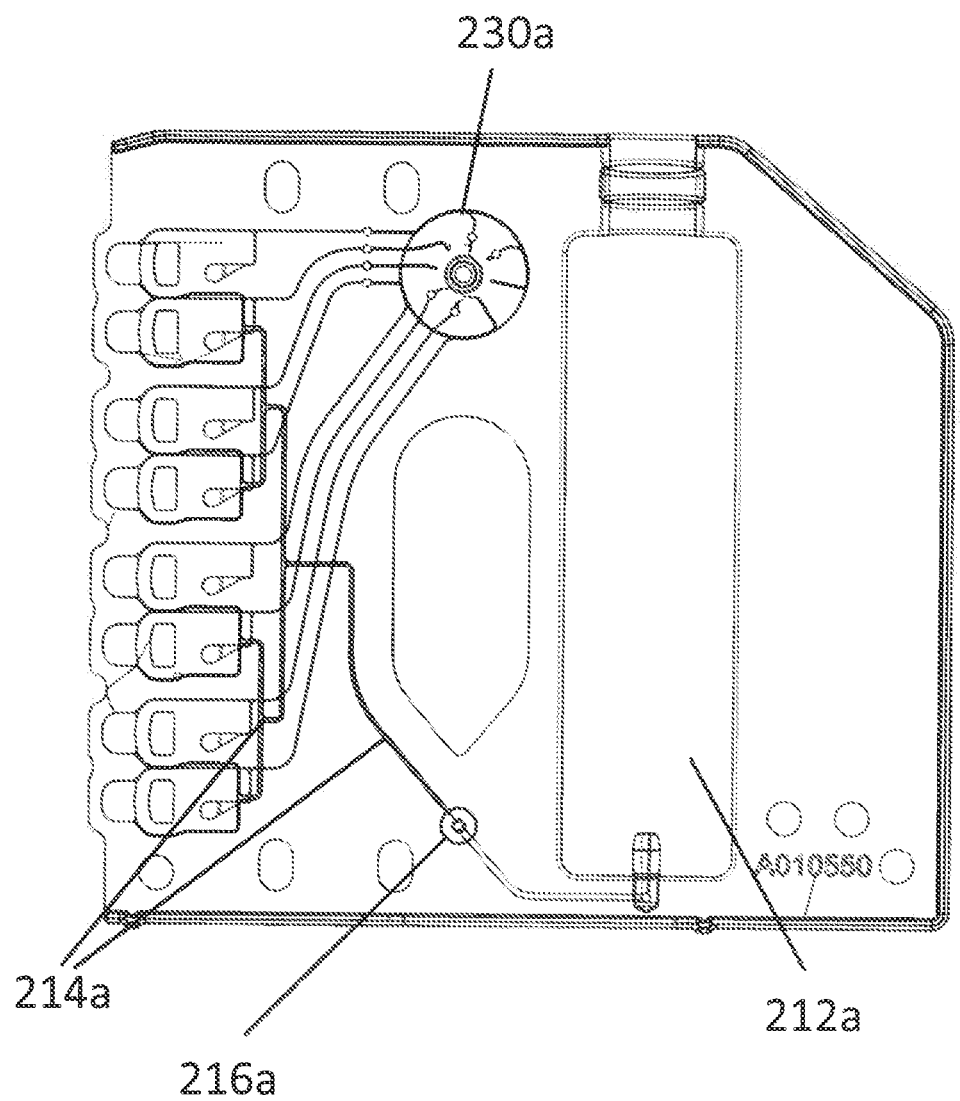
FIG. 24 shows an alternative embodiment of the hydrophobic valve.

In an alternated embodiment, the layout of hydrophobic junction valve 230 can be arranged as in FIG. 24 which shows an alternative layout of hydrophobic junction valve 230a.

Figure 25:
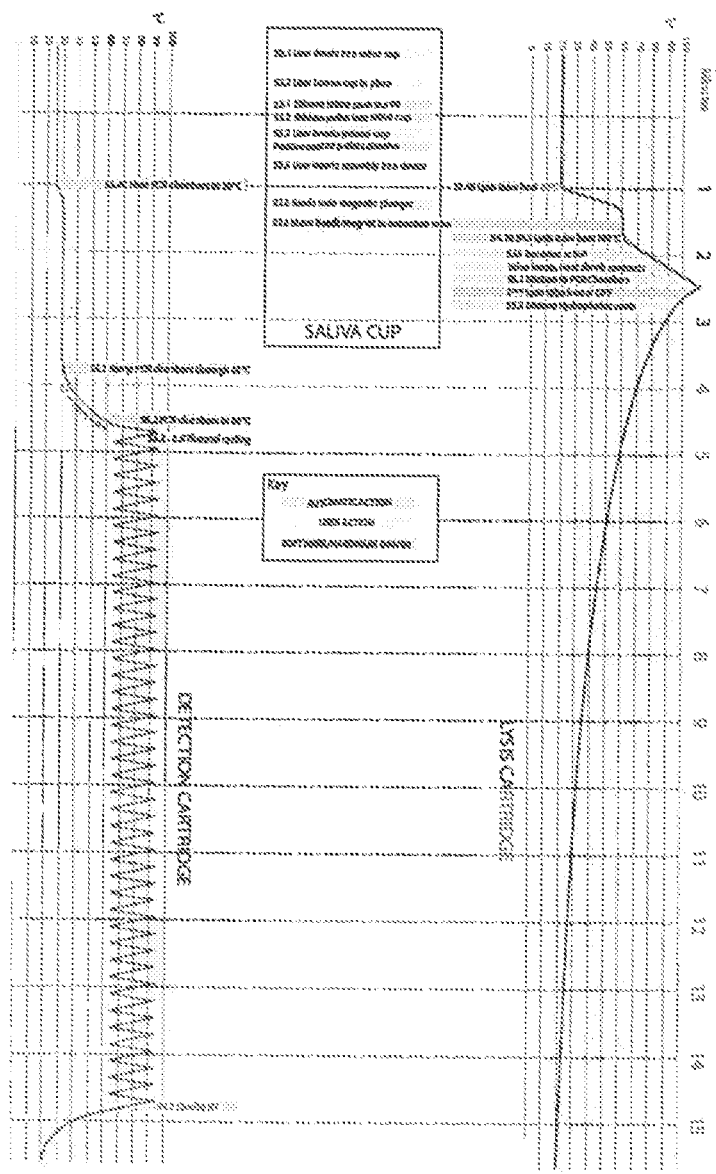
FIG. 25 shows a schematic flow chart of the assay steps used within an embodiment of the invention.

FIG. 25 shows a schematic chart of the user actions, temperature and fluidic flow control of an embodiment of the device of the present invention in use. In a preferred embodiment, a method of using the microfluidic device of the present invention comprises the following steps:

i. User/s deposits saliva sample in collection cup 12 or cup 112 which is connected to extraction tube 240.
ii. User connects cap 22 or cap 122 to cup 12 of cup 112 causing sealed cup and blister 24 or blister 224 to burst and release capture particles 28 such as magnetic capture beads with a means of capturing target compound virus.
iii. User initiates mixing of cup contents, at this stage, pelleted substance 43, if present, can dissolve into the sample.
iv. User inserts cup 12 of cup 112 and connected extraction tube 240 into cartridge 210 into aperture 212, forming the cartridge assembly 111, the cartridge assembly 111 is then inserted into housing 401 of detection control device 400.

v. Once the cartridge assembly 111 is inserted into housing 401 of detection control device 400, the subsequent processes are all automated, controlled by the detection device.

vi. The magnetic capture beads, having captured virus from a sample are attracted by the magnet within the cup and moved through by the magnet to extraction tube 240, containing extraction reagent. This magnet movement is achieved by action of plunger 38 or plunger 138 within cup 12. A piston within control device 400 may action the plunger controlled by timing software within the device 400.

vii. Extraction tube 240 is heated sufficiently to activate the extraction reagent which may be a thermostable enzyme, pre-filled within extraction tube 240.

viii. Heating causes extraction tube 240 which is at least partially formed from a heat-deformable material, to contract. The results of this action causes a pinch-valve within the cartridge to open, allowing the liquid through into cartridge microfluidic channels 214.

ix. A polymer filter sits above the interface within microfluidic cartridge 200. The liquid sample travels through this filter.

x. The heat-deformable material of the extraction tube continues to contract and effectively acts as a pump, the pressure pushing air behind the sample. The sample is forced through cartridge microfluidic channels 214 and up to the vertically stacked chambers 220.

xi. The sample is pushed through the polymer filter, and inlet valve 216 which sits close to the tube and cartridge interface 213. The inlet valve prevents sample flowing back through to extraction tube 240.

xii. The contraction from the deforming of extraction tube 240 and reduced internal volume, retains residual pressure which prevents any sample from falling back into extraction tube 240 due to gravity.

xiii. Cartridge channels 214 in microfluidic cartridge 200 branch off, leading to separate amplification chambers 220 stacked vertically.

xiv. Chambers 220 which can be used for PCR, fill in order depending on which cartridge channel 214 has the least resistance to fluid flow.

xv. The liquid continues to flow from PCR hydrophobic junction valve 230 within the cartridge.

xvi. Hydrophobic junction valve 230 provides hydrophobic membrane 232 which does not allow any liquid though, only air.

xvii. When liquid has filled PCR chambers 220 and units 234 of the hydrophobic junction valve, closure of ring-shaped valves 230 and inlet valve 216 occurs. Valve closure is automated by the device and can be automated based on detection of liquid or time-automated.

xviii. Chambers 220 within the cartridge will be heated and cooled by the thermocycling and heaters within the detection control device 400 and this will cause the amount of liquid in each chamber 220 to expand and contract.

xix. A hydrophobic sheet can sit above hydrophobic junction valve 230 which acts to prevent biohazardous vapor produced during the heating stage to escape microfluidic cartridge 200.

xx. At the point of valve closure, cartridge channels 214 are entirely full of liquid and thermocycling can begin.

xxi. The heating and cooling source of chambers 220 can be situated on either side of microfluidic cartridge 200 and the detection viewed by user or device via the edge of the cartridge face.

xxii. In the preferred embodiment, a single detector will scan all chambers, alongside the heating and cooling. The detector can be a fluorometer.

xxiii. The device algorithm and software within control device 400 provides the result based on the detection and analysis.

xxiv. The device may indicate a positive or negative presence of target biological compounds, pathogens or virus such as SARS-CoV-2 associated with disease COVID-19 and Influenza Types A and B xxv. The result may be displayed on a device user interface or may be transmitted via a data receiver.

xxvi. After detection is complete, microfluidic cartridge 200 is configured to be removed from detection device and disposed of in biohazardous waste.

It will be appreciated that other suitable amplification techniques can be used within chambers 220 with alternative thermocycling provided by the detection device 400.

In one embodiment, cup 12 or cup 112 is pre-inserted into microfluidic cartridge 200, prior to sample collection by the user. In this embodiment the user will be provided the saliva cup pre-inserted into microfluidic cartridge 200.

In an alternative embodiment, valve 230*a* is arranged in a layout as shown in FIG. 24. In this embodiment, a hydrophobic membrane is also situated above at least a portion of valve 230*a*, which stops the fluidic flow. The arrangement in 230*a* creates a region of high-resistance, stopping the liquid, until increased pressure from all eight channels being filled forces the liquid against the hydrophobic membrane. In this embodiment, both an inlet valve and valve 230*a* will be closed at the same time to begin PCR thermocycling.

Microfluidic cartridge 200 can be produced in any suitable materials, the material may be partially or fully transparent. In alternative embodiments chambers 220 can be stacked diagonally or horizontally. The entire microfluidic cartridge 200 can be used within a horizontal orientation instead of vertical or at any suitable degree or angle, meaning the stacked chambers 220 and extraction tube interface will be in the horizontal plane or resulting plane associated with the degree or angle of use. In this embodiment, the device will function in the same way as previously described.

In various alternative embodiments, the sample to be collected and analyzed may be saliva, blood, urine, tissue, plant tissue or any biological matter from one or more users or sources. If the sample is from multiple sources, for example the saliva from multiple individuals can be pooled together within the cup and processed and analyzed simultaneously, the device will work in the same way, with a positive result indicating that any individual from the sample pool may have the positive result and each individual from the pool being re-tested on an individual basis for identification purposes.

In various other alternative embodiments, the device is configured to prevent biohazardous waste and vapor from exiting the device.

In a further alternative embodiment, opening 212 of the cartridge may extend to surround the entirety of collection cup 12 or cup 112.

The disclosed apparatus and systems may also be said broadly to consist in the parts, elements and features referred to or indicated in the specification of the application, individually or collectively, in any or all combinations of two or more of said parts, elements or features.

It is to be understood that the above described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed:

1. A sample collection and processing device comprising:
a cup having an opening configured for collecting a sample;
a substance comprising capture particles within an interior of said cup, the capture particles capturing at least a portion of the sample with said cup; and
attraction means for attracting the capture particles capturing at least a portion of the sample, the attraction means is a magnet;
said attraction means moving said capture particles capturing at least a portion of the sample directly from said cup to an attachment tube, said attachment tube configured for attachment to a processing device.

2. The sample collection and processing device according to claim 1 wherein the substance is contained in an openable compartment within an interior of said cup and further comprising a piercing mechanism for opening the openable compartment to release the substance, the openable component is a blister, the capture particles of the substance comprises magnetic capture beads, wherein upon opening of the openable compartment the magnetic capture beads capture and bind to the at least one portion of the sample.

3. The sample collection and processing device according to claim 2 further comprising a cap, the cap configured to close the opening in the cup, said piercing mechanism is actioned by attachment of said cap to said opening, said piercing mechanism opening said blister.

4. The sample collection and processing device according to claim 3 wherein the cap comprises a central extruding portion housing a plunger mounted movably within the central extruding portion; the plunger comprising a base and an upper surface.

5. A sample collection and processing device comprising:
a cup having an opening configured for collecting a sample;
a substance comprising capture particles within an interior of said cup, the capture particles capturing at least a portion of the sample;
attraction means for attracting the capture particles capturing at least a portion of the sample, the attraction means is a magnet; said attraction means moving said capture particles capturing at least a portion of the sample to an attachment tube, said attachment tube configured for attachment to a processing device; and a cap, the cap configured to close the opening in the cup, the cap comprises a central extruding portion housing a plunger mounted movably within the central extruding portion, the plunger comprising a base and an upper surface wherein the base of the plunger is configured to contact said attraction means for moving said attraction means into said attachment tube.

6. A sample collection and processing device comprising:
a cup having an opening configured for collecting a sample;
a substance comprising capture particles within an interior of said cup, the capture particles capturing at least a portion of the sample;
attraction means for attracting the capture particles capturing at least a portion of the sample, the attraction means is a magnet, said attraction means moving said capture particles capturing at least a portion of the sample to an attachment tube, said attachment tube configured for attachment to a processing device; and
a cap, the cap configured to close the opening in the cup, the cap comprises a central extruding portion housing a plunger mounted movably within the central extruding portion, the plunger comprising a base and an upper surface wherein said upper surface of said plunger is configured to seal to said cup.

7. A sample collection and processing device comprising:
a cup having an opening configured for collecting a sample, a substance comprising capture particles within an interior of said cup, the capture particles capturing at least a portion of the sample, the capture particles of the substance; attraction means for attracting the capture particles capturing at least a portion of the sample, the attraction means is a magnet; said attraction means moving said capture particles capturing at least a portion of the sample to an attachment tube, said attachment tube configured for attachment to a processing device, the substance is contained in an openable compartment within an interior of said cup; a piercing mechanism for opening the openable compartment to release the substance, the openable component is a blister wherein the cup comprises an upper compartment and a lower compartment, said blister positioned in said upper compartment, said attraction means positioned in or integral with said lower compartment.

8. The sample collection and processing device according to claim 7 wherein the plunger is activated for moving said magnet into the attachment tube.

9. A sample collection and processing device comprising;
a cup having an opening configured for collecting a sample;
a substance comprising capture particles within an interior of said cup, the capture particles capturing at least a portion of the sample, the capture particles of the substance comprises magnetic capture beads; and attraction means for attracting the capture particles capturing at least a portion of the sample, the attraction means is a magnet; said attraction means moving said capture particles capturing at least a portion of the sample to an attachment tube, said attachment tube configured for attachment to a processing device; a cap, the cap configured to close the opening in the cup, the cap comprises a central extruding portion housing a plunger mounted movably within the central extruding portion, the plunger comprising a base and an upper surface further comprising a nest compartment positioned below said plunger, wherein said nest compartment is configured to hold a pelleted substance.

10. The sample collection and processing device of claim 1 wherein the attachment tube is at least partially formed of a heat deformable material.

11. The sample collection and processing apparatus according to claim 1 wherein said processing device is a micro-fluidic cartridge configured for nucleic acid amplification.

12. A microfluidic cartridge comprising:
a planar surface;
a cartridge opening positioned within the same plane as the planar surface, the cartridge opening configured for insertion of an attachment tube;

a plurality of microfluidic channels connecting said attachment tube to a plurality of chambers; and a junction valve comprising a plurality of units, each of the plurality of units leading to one of the plurality of chambers.

13. The microfluidic cartridge of claim 12 further comprising an inlet valve within the planar surface, said inlet valve closes a connection between said attachment tube and said plurality of microfluidic channels.

14. The microfluidic cartridge of claim 12 wherein the junction valve is at least partially covered by a hydrophobic membrane.

15. The microfluidic cartridge of claim 12 wherein each of the plurality of chambers is configured to receive reagents.

16. The microfluidic cartridge of claim 12 configured for insertion into a control detection device, the control detection device controlling:

a) a temperature of said microfluidic cartridge and b) valve closure; and the chamber windows of said microfluidic cartridge being transparent to detect results.

17. A kit comprising a sample collection device and a microfluidic cartridge;

said sample collection device comprising a cup having an opening configured for collecting a sample, a substance comprising capture particles within an interior of said cup, the capture particles able to capture at least a portion of the sample, an attraction means for attracting the capture particles, the attraction means is a magnet;

said attraction means moving said capture particles having captured at least a portion of the sample to an attachment tube;

said cartridge comprising a planar surface, a cartridge opening positioned vertically within the same plane as the planar surface, the cartridge opening configured for insertion of the attachment tube, a plurality of microfluidic channels connecting said attachment tube to a plurality of chambers, and a junction valve comprising a plurality of units, each of the plurality of units leading to one of the plurality of chambers wherein the junction valve is configured to provide flow of the captured portion of the sample in the attachment tube to one of the plurality of chambers.

* * * * *